US010294282B2

(12) United States Patent
Ikeuchi

(10) Patent No.: US 10,294,282 B2
(45) Date of Patent: May 21, 2019

(54) ANTIBODY CAPABLE OF BINDING TO INTRANUCLEAR PROTEIN OF INFLUENZA VIRUS, COMPOSITE, DETECTION DEVICE AND METHOD USING SAME

(71) Applicant: Panasonic Intellectual Property Management Co., Ltd., Osaka (JP)

(72) Inventor: Emina Ikeuchi, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/054,231

(22) Filed: Aug. 3, 2018

(65) Prior Publication Data

US 2019/0077836 A1 Mar. 14, 2019

(30) Foreign Application Priority Data

Sep. 12, 2017 (JP) ................................. 2017-174900

(51) Int. Cl.

*C07K 16/08* (2006.01)
*C07K 14/11* (2006.01)
*G01N 33/543* (2006.01)
*G01N 33/533* (2006.01)
*G01N 33/569* (2006.01)

(52) U.S. Cl.

CPC ............ *C07K 14/11* (2013.01); *G01N 33/533* (2013.01); *G01N 33/5436* (2013.01); *C07K 2317/565* (2013.01); *C07K 2317/76* (2013.01); *G01N 33/56983* (2013.01)

(58) Field of Classification Search

None

See application file for complete search history.

(56) References Cited

U.S. PATENT DOCUMENTS 9,771,415 B2 9/2017 Hufton
9,868,778 B2 1/2018 Muraoka

OTHER PUBLICATIONS

Zabetakis et al., PLOS ONE vol. 8, No. 10, e77678, 2013.*
MacCallum et al. J. Mol. Biol. (1996) 262, 732-745.*

* cited by examiner

*Primary Examiner* — Shanon A. Foley
*Assistant Examiner* — Myron G Hill
(74) *Attorney, Agent, or Firm* — McDermott Will & Emery LLP

(57) ABSTRACT

The present invention is an antibody including an amino acid sequence, wherein the amino acid sequence includes, in an N- to C-direction, the following structural domains:

N-FR1-CDR1-FR2-CDR2-FR3-CDR3-FR4-C wherein

FR denotes a framework region amino acid sequence and CDR denotes a complementary determining region amino acid sequence;

the CDR1 includes an amino acid sequence represented by SEQ ID NO: 1;

the CDR2 includes an amino acid sequence represented by SEQ ID NO: 2;

the CDR3 includes an amino acid sequence represented by SEQ ID NO: 3; and the antibody is capable of binding to an intranuclear protein of an influenza virus.

8 Claims, 17 Drawing Sheets

Specification includes a Sequence Listing.

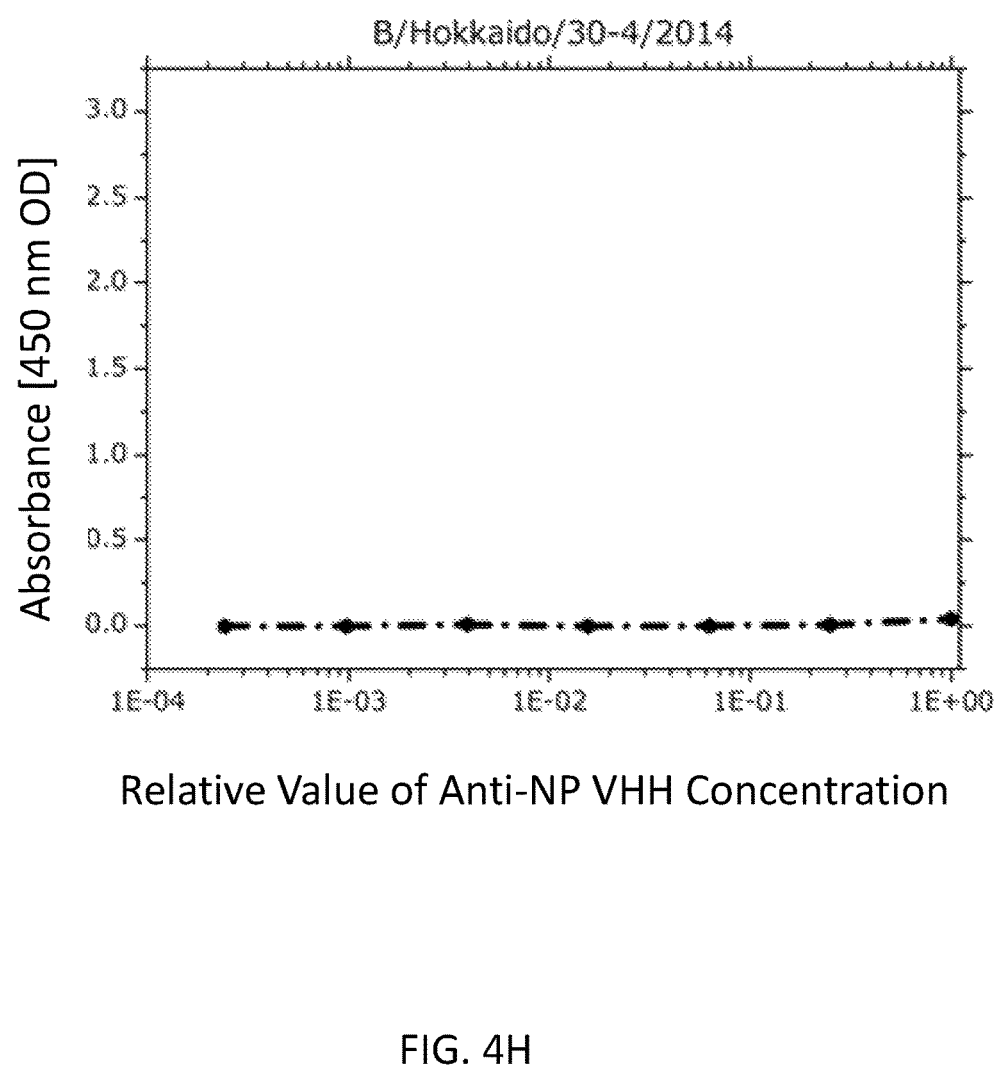

B/Hokkaido/30-4/2014

Absorbance [450 nm OD]

3.0
2.5
2.0
1.5
1.0
0.5
0.0

1E-04 1E-03 1E-02 1E-01 1E+00

Relative Value of Anti-NP VHH Concentration

FIG. 4H

ANTIBODY CAPABLE OF BINDING TO INTRANUCLEAR PROTEIN OF INFLUENZA VIRUS, COMPOSITE, DETECTION DEVICE AND METHOD USING SAME

INCORPORATION BY REFERENCE-SEQUENCE LISTING

The material contained in the ASCII text file named "P1009397US01_ST25.txt" created on May 31, 2018 and having a file size of 20, 601 bytes is incorporated by reference herein.

BACKGROUND

1. Technical Field

The present invention relates to an antibody capable of binding to an intranuclear protein of an influenza virus, a composite, a detection device and method using the same.

2. Description of the Related Art

Patent Literature 1 and Patent Literature 2 disclose antibodies each capable of binding to an influenza virus. At least a part of the antibodies disclosed in Patent Literature 1 and Patent Literature 2 is derived from an alpaca. Patent Literature 1 and Patent Literature 2 are incorporated herein by reference.

CITATION LIST

Patent Literature

Patent Literature 1
U.S. Pat. No. 9,771,415
Patent Literature 2
U.S. Pat. No. 9,868,778

SUMMARY

An object of the present invention is to provide a novel antibody capable of binding to an intranuclear protein of an influenza virus, a composite, a detection device and method using the same.

The present invention is an antibody including an amino acid sequence, wherein the amino acid sequence includes, in an N- to C-direction, the following structural domains:

N-FR1-CDR1-FR2-CDR2-FR3-CDR3-FR4-C wherein

FR denotes a framework region amino acid sequence and CDR denotes a complementary determining region amino acid sequence;

the CDR1 includes an amino acid sequence represented by SEQ ID NO: 1;

the CDR2 includes an amino acid sequence represented by SEQ ID NO: 2;

the CDR3 includes an amino acid sequence represented by SEQ ID NO: 3; and the antibody is capable of binding to an intranuclear protein of a type-A influenza virus.

The present invention provides a novel antibody capable of binding to an intranuclear protein of an influenza virus. The present invention also provides a composite comprising the novel antibody. The present invention further provides a detection device and a detection method using the novel antibody.

BRIEF DESCRIPTION OF THE DRAWINGS

FIG. 4H is a graph showing a measurement result of a cross reactivity of the VHH antibody including the amino acid sequence represented by SEQ ID NO: 8 with a type-B influenza virus B/Hokkaido/30-4/2014.

DETAILED DESCRIPTION OF THE EMBODIMENT

Figure 1A:
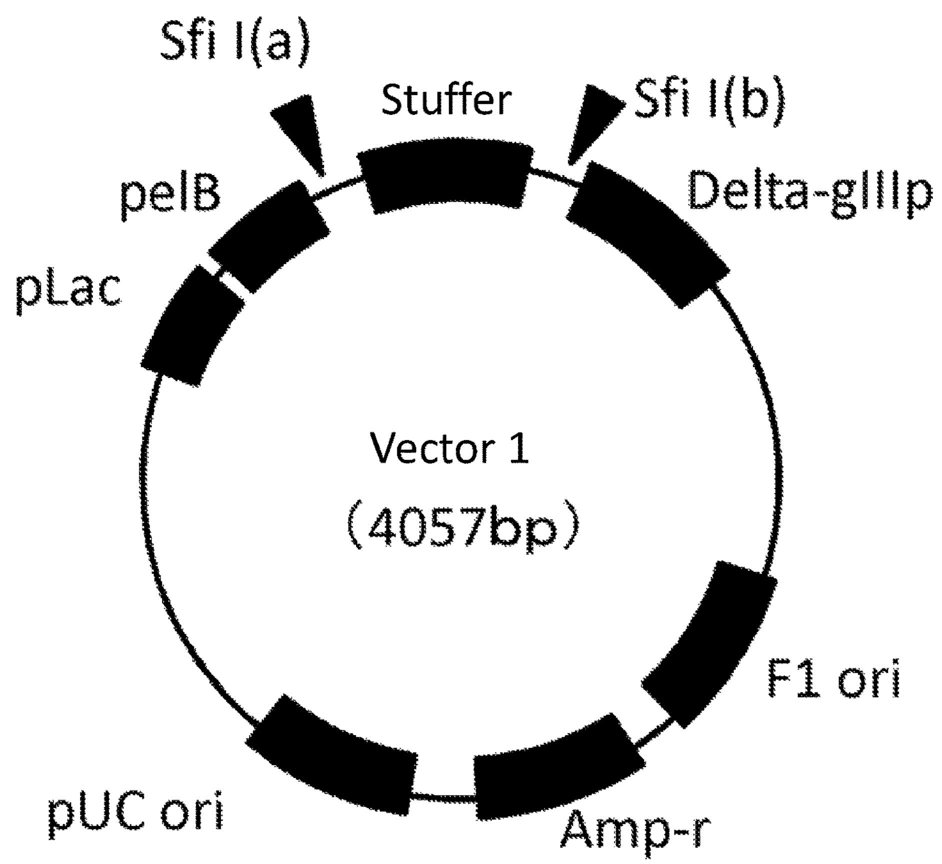
FIG. 1A is a vector map used to ligate various genes included in a gene library of a VHH antibody.

The antibody according to the present invention is capable of binding to a type-A influenza virus. In particular, the antibody according to the present invention is capable of binding to an intranuclear protein of the type-A influenza virus. As disclosed in Patent Literature 1, an antibody capable of binding to an influenza virus includes an amino acid sequence including, in an N- to C-direction, the following structural domains.

N-FR1-CDR1-FR2-CDR2-FR3-CDR3-FR4-C wherein

FR denotes a framework region amino acid sequence and CDR denotes a complementary determining region amino acid sequence.

In the present invention, the CDR1 includes an amino acid sequence represented by DRTDSNYAMG (SEQ ID NO: 1)

In the present invention, the CDR2 includes an amino acid sequence represented by AISGTGYVTGYADSARN (SEQ ID NO: 2).

In the present invention, the CDR3 includes an amino acid sequence represented by TSDQRYPGPRSSGYDY (SEQ ID NO: 3).

Desirably, the CDR1, the CDR2, and the CDR3 are represented by SEQ ID NO: 1, SEQ ID NO: 2, and SEQ ID NO: 3, respectively. In this case, more desirably, the FR1, the FR2, the FR3, and the FR4 includes amino acid sequences represented by QVQLVESGGGLVQTGGPLRLSCAVS (SEQ ID NO: 4), WFRQAPGKEREFVA (SEQ ID NO: 5), RFTLSRDNGKNAVYLQMNSLEPADTAVYYCAA (SEQ ID NO: 6), and WGQGTQVTVSS (SEQ ID NO: 7), respectively.

In other words, it is desirable that the antibody according to the present invention includes the amino acid sequence represented by (SEQ ID NO: 8)
QVQLVESGGGLVQTGGPLRLSCAVSDRTDSNYAMGWFRQAPGKEREFVAAI
SGTGYVTGYADSARNRFTLSRDNGKNAVYLQMNSLEPADTAVYYCAATSDQ
RYPGPRSSGYDYWGQGTQVTVSS.

The antibody including the amino acid sequence represented by SEQ ID NO: 8 does not have antigen cross reactivity with influenza viruses other than a type-A influenza virus. An example of the influenza viruses other than a type-A influenza virus is a type-B influenza virus.

Note that "include" includes "consist of" and "essentially consist of" in the present specification.

The antibody according to the present invention can be employed in a detection device or in a detection method for detecting the intranuclear protein of the type-A influenza virus. In this case, the antibody according to the present invention may be used in a state of a composite bound to another material, for example, in a state of a composite in which the antibody according to the present invention has been bound to at least one selected from the group consisting of a solid phase support and a labeled substance.

As long as the solid phase support is a support insoluble in a solvent used for a reaction system of an antigen-antibody reaction, a shape and a material of the solid phase support is not limited. An example of the shape of the solid phase support is a plate, a bead, a disk, a tube, a filter, and a film. An example of a material of the solid phase support is a polymer such as polyethylene terephthalate, cellulose acetate, polycarbonate, polystyrene, or polymethylmethacrylate, a metal such as gold, silver, or aluminum, or glass. A known method such as a physical adsorption method, a covalent binding method, an ion bonding method, or a cross-linking method is employed as a method for binding the antibody to the solid phase support.

For example, a labeled substance such as a fluorescent substance, a luminescent substance, a dye, an enzyme, or a radioactive substance is used. A known method such as a physical adsorption method, a covalent binding method, an ion bonding method, or a cross-linking method is employed as a method for binding the antibody to the labeled substance.

In the detection method in which the antibody according to the present invention is used, the composite including the antibody is brought into contact with an analyte. Then, detected is a change of a physical amount based on an antigen-antibody reaction of the intranuclear protein of the type-A influenza virus contained in the analyte and the antibody included in the composite. An example of the physical amount is luminescence intensity, chromaticity, light transmission, turbidness, absorbance, or radiation dose. A known method such as an enzyme immunoassay method, an immunochromatography method, a latex agglutination method, a radioimmunoassay method, a fluorescence immunoassay method, or a surface plasmon resonance spectroscopy method is employed as a specific example of the detection method.

The detection device in which the antibody according to the present invention is employed includes a detector for detecting any one of the physical amount which is changed on the basis of the antigen-antibody reaction. The detector is composed of a known device such as a photometer, a spectroscope, or a dosimeter.

The antibody may be used not only as a composite bound to another material but also as a composition including the antibody according to the present invention or as a kit including the antibody according to the present invention.

EXAMPLES

Inventive Example 1

VHH antibodies (i.e., a variable domain of a heavy chain of a heavy chain antibody) capable of binding to an intranuclear protein included in a type-A influenza virus H1N1 were prepared in accordance with the following procedures. Hereinafter, the intranuclear protein is referred to as "NP".

(Immunization of Alpaca and Acquirement of Mononuclear)

In order to forma VHH antibody gene library, an alpaca was immunized using a recombinant intranuclear protein (SEQ ID NO: 24) derived from a type-A influenza virus H1N1 (A/Puerto Rico/8/34/Mount Sinai) as an antigen. The recombinant intranuclear protein was prepared using a *Brevibacillus* expression system by Higeta Shoyu Co., Ltd. The recombinant intranuclear protein was prepared with an adjuvant before administrated to an alpaca.

The recombinant intranuclear protein (SEQ ID NO: 24) used in the inventive example 1 is shown below.

```
(SEQ ID NO: 24)
MASQGTKRSYEQMETDGERQNATEIRASVGKMIGGIGRFYIQMCTELKLSD

YEGRLIQNSLTIERMVLSAFDERRNKYLEEHPSAGKDPKKTGGPIYRRVNG

KWMRELILYDKEEIRRIWRQANNGDDATAGLTHMMIWHSNLNDATYQRTRA

LVRTGMDPRMCSLMQGSTLPRRSGAAGAAVKGVGTMVMELVRMIKRGINDR

NFWRGENGRKTRIAYERMCNILKGKFQTAAQKAMMDQVRESRNPGNAEFED

LTFLARSALILRGSVAHKSCLPACVYGPAVASGYDFEREGYSLVGIDPFRL

LQNSQVYSLIRPNENPAHKSQLVWMACHSAAFEDLRVLSFIKGTKVLPRGK

LSTRGVQIASNENMETMESSTLELRSRYWAIRTRSGGNTNQQRASAGQISI

QPTFSVQRNLPFDRTTIMAAFNGNTEGRTSDMRTEIIRMMESARPEDVSFQ

GRGVFELSDEKAASPIVPSFDMSNEGSYFFGDNAEEYDN
```

Specifically, the recombinant intranuclear protein having a concentration of 100 micrograms/milliliter was administered to the alpaca. After one week, the recombinant intranuclear protein having the same concentration was administered to the alpaca, again. In this way, the alpaca was immunized with the recombinant intranuclear protein five times for five weeks. After another week, blood of the alpaca was extracted. Then, mononuclear cells were acquired from the blood as below.

A blood cell separation solution (available from COSMO BIO Co., Ltd., trade name: Lymphoprep) was added to a lymphocyte separation tube (available from Greiner Bio-One Co., Ltd., trade name: Leucosep). Then, the solution was subjected to centrifugation at a temperature of 20 degrees Celsius at 1,000×g for one minute.

The blood extracted from the alpaca was treated with heparin. Then, an equivalent amount of phosphate buffered saline (hereinafter, referred to as "PBS") was added to the thus-treated blood to obtain a sample solution. Then, the sample solution was added to the lymphocyte separation tube containing the blood cell separation solution.

The lymphocyte separation tube was subjected to centrifugation at a temperature of 20 degrees Celsius at 800×g for thirty minutes.

A fraction containing the mononuclear cells was collected. PBS three times in volume was added. The fraction was subjected to centrifugation at a temperature of 20 degrees Celsius at 300×g for five minutes. The precipitate was suspended with PBS gently. After the suspending, 10 microliters of the suspension was separated in order for the count of the number of cells. The remaining suspension was subjected to centrifugation at a temperature of 20 degrees Celsius at 300×g for five minutes.

An RNA storage solution (trade name: RNAlater) having a volume of 2 milliliters was added to the precipitate. Then, the solution was suspended gently. The suspension was injected into two tubes each having a volume of 1.5 milliliters. Each tube included 1 milliliter of the suspension. The tube was stored at a temperature of −20 degrees Celsius. The suspension (5 microliters) separated for the count of the number of cells was mixed with a Turk's solution (15 microliters), and the number of the mononuclear cells was counted with a counting chamber.

(Formation of cDNA Gene Library of VHH Antibody)

Then, a total RNA was extracted from the mononuclear cells, and a cDNA gene library of the VHH antibody was formed in accordance with the following procedure. In the following procedure, RNase-free-grade reagents and instruments were used.

A total RNA isolation reagent (trade name: TRIzol Reagent, 1 milliliter) was added to the mononuclear cell fraction. The reagent was mixed gently and left at rest at room temperature for five minutes. Chloroform (200 microliters) was added to the reagent, and the reagent was shaken strongly for fifteen seconds. The reagent was left at rest at room temperature for two-three minutes. The reagent was subjected to centrifugation at 12,000×g or less at a temperature of 4 degrees Celsius for 15 minutes.

The supernatant was moved to a new tube. RNase-free water and chloroform (200 microliters, each) were added to the tube. In addition, 500 milliliters of isopropanol was added to the tube. The liquid contained in the tube was stirred with a vortex mixer. The liquid was left at rest at room temperature for ten minutes. Then, the liquid was subjected to centrifugation at 12,000×g or less at a temperature of 4 degrees Celsius for fifteen minutes. The supernatant was removed, and the precipitate was rinsed with one milliliter of 75% ethanol. This solution was subjected to centrifugation at 7,500×g or less at a temperature of four degrees Celsius for five minutes. The solution was dried to obtain total RNA. The obtained total RNA was dissolved in RNase-free water.

In order to obtain cDNA from the total RNA, a kit including a reverse transcriptase was employed. The kit was available from Takara Bio Inc., as a trade name of PrimeScript II $1^{st}$ strand cDNA Synthesis Kit. The Random 6 mer and Oligo dT primer included in the kit were used as primers. The cDNA was obtained in accordance with the standard protocol attached to the kit.

The gene of the VHH antibody included in the alpaca was obtained from the cDNA by a PCR method. An enzyme for PCR was available from Takara Bio Inc., as a trade name of Ex-taq.

The following reagents were mixed to obtain a mixture solution.

| | |
|---|---|
| 10× buffer | 5 microliters |
| dNTPs | 4 microliters |
| Primer F | 2 microliters |
| Primer R | 2 microliters |
| cDNA template | 1 microliter |
| Ex-taq | 0.25 microliters |

The mixture solution was subjected to the following PCR method.

First, the mixture solution was heated at a temperature of 95 degrees Celsius for two minutes.

Then, the temperature of the mixture solution was varied in accordance with the following cycle.

Ninety six degrees Celsius for thirty seconds,

Fifty two degrees Celsius for thirty seconds, and

Sixty eight degrees Celsius for forty seconds

This cycle was repeated thirty times.

Finally, the mixture solution was heated at a temperature of sixty eight degrees Celsius for four minutes and stored at a temperature of four degrees Celsius.

The following primers were used in the present PCR method.

```
Primer 1:
(SEQ ID NO: 9)
5'-GGTGGTCCTGGCTGC-3'

Primer 2:
(SEQ ID NO: 10)
5'-ctgctcctcgcGGCCCAGCCGGCCatggcTSAGKTGCAGCTCGTGGA
GTC-3'
```

Primer 3:
(SEQ ID NO: 11)
5'-TGGGGTCTTCGCTGTGGTGCG-3'

Primer 4:
(SEQ ID NO: 12)
5'-TTGTGGTTTTGGTGTCTTGGG-3'

Primer 5:
(SEQ ID NO: 13)
5'tttgCtctGCGGCCGCagaGGCCgTGGGGTCTTCGCTGTGGTGCG-3'

Primer 6:
(SEQ ID NO: 14)
5'tttgCtctGCGGCCGCagaGGCCgaTTGTGGTTTTGGTGTCTTGGG-3'

(Reference literature: Biomed Environ Sci., 2012; 27(2): 118-121)

Three PCR assays were conducted.

In the first PCR assay, a primer set A composed of the cDNA, Primer 1 and Primer 3 and a primer set B composed of the cDNA, Primer 1 and Primer 4 were used.

In the second PCR assay, a primer set C composed of the gene amplified with the primer set A, Primer 2, and Primer 3, and a primer set D composed of the gene amplified with the primer set B, Primer 2, and Primer 4 were used.

In the third PCR assay, a primer set E composed of the gene amplified with the primer set C, Primer 2, and Primer 5, and a primer set F composed of the gene amplified with the primer set D, Primer 2, and Primer 6 were used.

In this way, the gene library of the VHH antibody was formed. In other words, the gene library of the VHH antibody included the genes amplified with the primer sets E and F.

(Formation of Phage Library)

Next, a phage library was formed from the gene library of the VHH antibody in accordance with the following procedures.

Figure 1B:
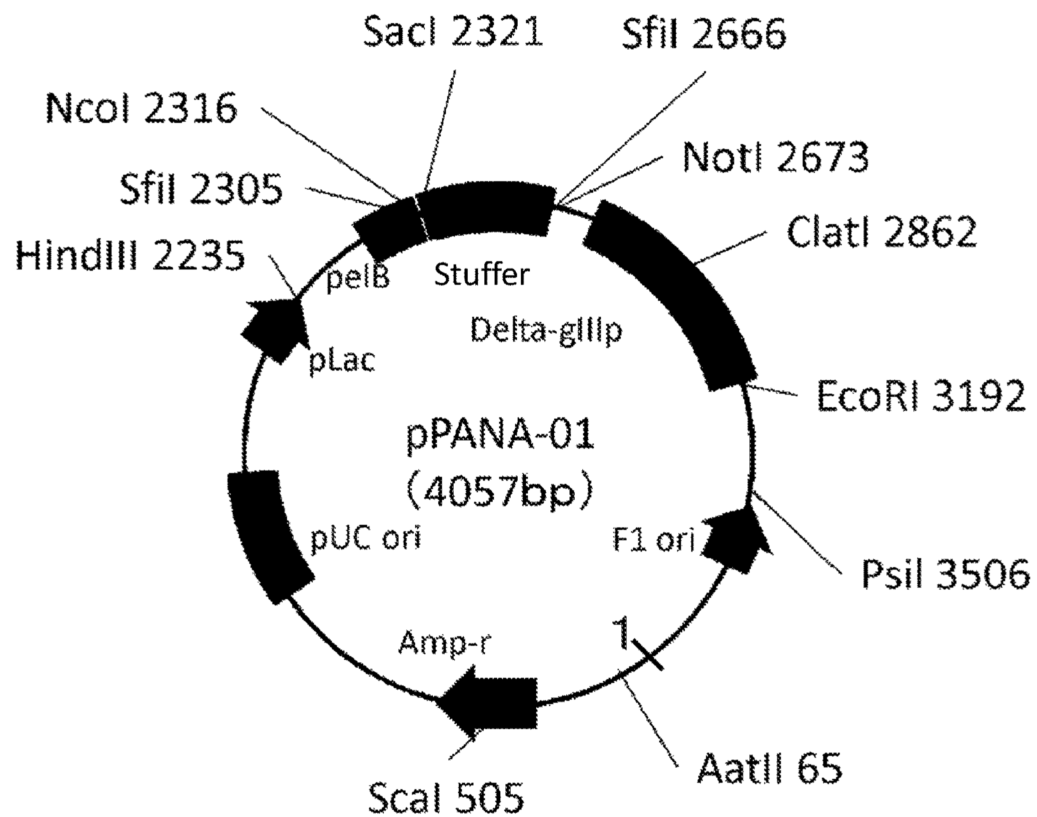
FIG. 1B shows the detail of the vector map shown in FIG. 1A.

A plasmid Vector 1 (4057 bp, see FIG. 1A) derived from a commercially available plasmid pUC119 (for example, available from Takara Bio Inc.) was treated with a restriction enzyme SfiI. The restriction enzyme site SfiI(a) shown in FIG. 1A consists of the gene sequence represented by GGCCCAGCCGGCC (SEQ ID NO: 15). The restriction enzyme site SfiI(b) consists of the gene sequence represented by GGCCTCTGCGGCC (SEQ ID NO: 16). FIG. 1B shows a detailed vector map of the plasmid Vector 1.

The plasmid Vector 1 consists of the following gene sequence.

(SEQ ID NO: 17)
gacgaaagggcctcgtgatacgcctatttttataggttaatgtcatgataa taatggtttcttagacgtcaggtggcacttttcggggaaatgtgcgcggaa cccctatttgtttatttttctaaatacattcaaatatgtatccgctcatga gacaataaccctgataaatgcttcaataatattgaaaaaggaagagtatga gtattcaacatttccgtgtcgcccttattcccttttttgcggcattttgcc ttcctgtttttgctcacccagaaacgctggtgaaagtaaaagatgctgaag atcagttgggtgcacgagtgggttacatcgaactggatctcaacagcggta agatccttgagagttttcgccccgaagaacgttttccaatgatgagcactt ttaaagttctgctatgtggcgcggtattatcccgtattgacgccgggcaag agcaactcggtcgccgcatacactattctcagaatgacttggttgagtact caccagtcacagaaaagcatcttacggatggcatgacagtaagagaattat gcagtgctgccataaccatgagtgataacactgcggccaacttacttctga caacgatcggaggaccgaaggagctaaccgcttttttgcacaacatgggg atcatgtaactcgccttgatcgttgggaaccggagctgaatgaagccatac caaacgacgagcgtgacaccacgatgcctgtagcaatggcaacaacgttgc gcaaactattaactggcgaactacttactctagcttcccggcaacaattaa tagactggatggaggcggataaagttgcaggaccacttctgcgctcggccc ttccggctggctggtttattgctgataaatctggagccggtgagcgtgggt ctcgcggtatcattgcagcactggggccagatggtaagccctcccgtatcg tagttatctacacgacggggagtcaggcaactatggatgaacgaaatagac agatcgctgagataggtgcctcactgattaagcattggtaactgtcagacc aagtttactcatatatactttagattgatttaaaacttcatttttaattta aaaggatctaggtgaagatcctttttgataatctcatgaccaaaatccctt aacgtgagttttcgttccactgagcgtcagaccccgtagaaaagatcaaag gatcttcttgagatcctttttttctgcgcgtaatctgctgcttgcaaacaa aaaaaccaccgctaccagcggtggtttgtttgccggatcaagagctaccaa ctctttttccgaaggtaactggcttcagcagagcgcagataccaaatactg tccttctagtgtagccgtagttaggccaccacttcaagaactctgtagcac cgcctacatacctcgctctgctaatcctgttaccagtggctgctgccagtg gcgataagtcgtgtcttaccgggttggactcaagacgatagttaccggata aggcgcagcggtcgggctgaacggggggttcgtgcacacagcccagcttgg agcgaacgacctacaccgaactgagatacctacagcgtgagctatgagaaa gcgccacgcttcccgaagggagaaaggcggacaggtatccggtaagcggca gggtcggaacaggagagcgcacgagggagcttccagggggaaacgcctggt atctttatagtcctgtcgggtttcgccacctctgacttgagcgtcgatttt tgtgatgctcgtcaggggggcggagcctatggaaaaacgccagcaacgcgg cctttttacggttcctggccttttgctggccttttgctcacatgttctttc ctgcgttatcccctgattctgtggataaccgtattaccgcctttgagtgag ctgataccgctcgccgcagccgaacgaccgagcgcagcgagtcagtgagcg aggaagcggaagagcgcccaatacgcaaaccgcctctccccgcgcgttggc cgattcattaatgcagctggcacgacaggtttcccgactggaaagcgggca gtgagcgcaacgcaattaatgtgagttagctcactcattaggcaccccagg ctttacactttatgcttccggctcgtatgttgtgtggaattgtgagcggat aacaatttcacacaggaaacagctatgaccatgattacgccAAGCTTCGAA GGAGACAGTCATAatgaaatacctgctgccgaccgctgctgctggtctgct gctcctcgcGGCCCAGCCGGCCatggagcTCAAGATGACACAGACTACATC

CTCCCTGTCAGCCTCTCTGGGAGACAGAGTCACCATCAGTTGCAGGGCAAG

TCAGGACATTAGCGATTATTTAAACTGGTATCAGCAGAAACCAGATGGAAC

TGTTAAACTCCTGATCTATTACACATCAAGTTTACACTCAGGAGTCCCATC

AAGGTTCAGTGGCGGTGGGTCTGGAACAGATTATTCTCTCACCATTAGCAA

-continued

```
CCTGGAGCAAGAAGATATTGCCACTTACTTTTGCCAACAGGGTAATACGCT
TCCGTGGACGTTTGGTGGAGGCACCAAGCTGGAAATCAAACGGGCTGATGC
TGCACCAACTgtaGGCCtctGCGGCCGCagaGcaaaaactcatctcagaag
aggatctgaatggggccgcaTAGggttccggtgattttgattatgaaaaga
tggcaaacgctaataagggggctatgaccgaaaatgccgatgaaaacgcgc
tacagtctgacgctaaaggcaaacttgattctgtcgctactgattacggtg
ctgctatcgatggtttcattggtgacgtttccggccttgctaatggtaatg
gtgctactggtgattttgctggctctaattcccaaatggctcaagtcggtg
acggtgataattcacctttaatgaataatttccgtcaatatttaccttccc
tccctcaatcggttgaatgtcgcccttttgtctttagcgctggtaaaccat
atgaattttctattgattgtgacaaaataaacttattccgtggtgtctttg
cgtttcttttatatgttgccacctttatgtatgtattttctacgtttgcta
acatactgcgtaataaggagtctTAATAAgaattcactggccgtcgtttta
caacgtcgtgactgggaaaaccctggcgttacccaacttaatcgccttgca
gcacatccccctttcgccagctggcgtaatagcgaagaggcccgcaccgat
cgcccttcccaacagttgcgcagcctgaatggcgaatggcgcctgatgcgg
tattttctccttacgcatctgtgcggtatttcacaccgCATATGaAAATTG
TAAgcgttaatattttgttaaaattcgcgttaaatttttgttaaatcagct
cattttttaaccaataggccgaaatcggcaaaatcccttataaatcaaaag
aatagaccgagatagggttgagtgttgttccagtttggaacaagagtccac
tattaaagaacgtggactccaacgtcaaagggcgaaaaaccgtctatcagg
gcgatggcccactacgtgaaccatcaccctaatcaagttttttggggtcga
ggtgccgtaaagcactaaatcggaaccctaaagggagcccccgatttagag
cttgacggggaaagccggcgaacgtggcgagaaaggaagggaagaaagcga
aaggagcgggcgctagggcgctggcaagtgtagcggtcacgctgcgcgtaa
ccaccacacccgccgcgcttaatgcgccgctacaGGGCGCGTcccatATGg
tgcactctcagtacaatctgctctgatgccgcatagttaagccagccccga
cacccgccaacacccgctgacgcgccctgacgggcttgtctgctcccggca
tccgcttacagacaagctgtgaccgtctccgggagctgcatgtgtcagagg
ttttcaccgtcatcaccgaaacgcgcga
```

Similarly, the gene library of the VHH antibody was treated with the restriction enzyme SfiI. In this way, VHH antibody gene fragments were obtained.

The thus-treated plasmid Vector 1 was mixed with the VHH antibody gene fragments at a ratio of 1:2. An enzyme (available from Toyobo Co. Ltd., trade name: Ligation High ver. 2) was injected into the mixture solution. The mixture solution was left at rest at a temperature of 16 degrees Celsius for two hours. In this way, each of the VHH antibody gene fragments was ligated into the plasmid Vector 1.

*Coli* bacteria (available from Takara Bio Inc., trade name: HST02) were transfected with the thus-ligated plasmid Vector 1.

Then, the *coli* bacteria were incubated for fifteen hours on a 2YT plate culture medium containing ampicillin at a concentration of 100 micrograms/milliliter. In this way, obtained was a library of phages each of which displays a protein obtained from the gene fragment included in the gene library of the VHH antibody.

After the incubation, a concentration of the library was calculated by counting the number of single colonies formed on the 2YT plate culture medium. As a result, the library of the phages had a concentration of $5\times10^7$/milliliter.

(Biopanning)

VHH antibodies capable of specifically binding to the intranuclear protein were obtained from the phage library in accordance with the following procedures.

In order to extract the clones each capable of binding to the antigen from among the phages which expressed the VHH antibody, biopanning was conducted twice.

*Coli* bacteria (HST02) into which the VHH antibody gene fragment included in the gene library of the VHH antibody was introduced were incubated at a temperature of 30 degrees Celsius in the 2YT AG culture medium containing 100 micrograms/milliliter of ampicillin and 1% glucose until a value $OD_{600}$ indicating absorbance reached 1.0. The 2YT AG culture medium has a volume of 100 milliliters. In this way, the *coli* bacteria were proliferated.

Helper phages (available from Invitrogen company, trade name: M13K07) were added to the *coli* bacteria culture medium in such a manner that the multiplicity of infection (MOI) was approximately 20.

Then, the culture medium was warmed at a temperature of 37 degrees Celsius for about thirty minutes. Then, the culture medium was subjected to centrifugation at a rotation speed of 4,000 rpm for ten minutes to collect the *coli* bacteria. The *coli* bacteria were incubated overnight at a temperature of 30 degrees Celsius in a 2YTAK culture medium (i.e., a 2YT culture containing 100 micrograms/milliliter of ampicillin and 50 micrograms/milliliter of kanamycin), while subjected to centrifugation at 213 rpm. The 2YTAK culture medium has a volume of 100 milliliters.

The incubation liquid (100 milliliters) containing the thus-incubated *coli* bacteria was injected into two centrifugation tubes (volume: 50 milliliters, each). The two centrifugation tubes were subjected to centrifugation at a rotation speed of 4,000 rpm for ten minutes. Then, the supernatants (20 milliliters, each) were collected.

The supernatants (40 milliliters) were added to a 20% polyethylene glycol solution (10 milliliters) containing NaCl (2.5 M). Then, the mixture solution was mixed upside down. Subsequently, the mixture solution was cooled on ice for approximately one hour. The mixture solution was subjected to centrifugation at a rotation speed of 4,000 rpm for ten minutes. Then, the supernatant was removed. PBS containing 10% glycerol was injected toward the precipitate. Finally, the precipitate was loosened and dissolved. In this way, a library of phages each of which displays the VHH antibody was obtained.

(Screening of VHH Antibody Capable of Specifically Binding to NP)

(A) Immobilization of NP Antigen

NP was mixed with PBS to prepare an NP solution. The concentration of NP was 2 micrograms/milliliter. The NP solution (2 milliliters) was injected into an immunotube (available from NUNC Co., Ltd.). The NP solution was left at rest in the immunotube overnight. In this way, NP was immobilized in the immunotube.

Then, the inside of the immunotube was washed three times with PBS.

The inside of the immunotube was filled with PBS which contained 3% skim milk (available from Wako Pure Chemical Industries, Ltd.). In this way, NP was blocked as an antigen in the immunotube.

The immunotube was left at rest at room temperature for one hour. Subsequently, the inside of the immunotube was washed three times with PBS.

(B) Panning

The library of the phages each of which displays the VHH antibody (concentration: approximately 5E+11/milliliter) was mixed with 3 milliliters of PBS containing 3% skim milk to prepare a mixture solution. The mixture solution was injected into the immunotube in which the NP antigen was immobilized.

A lid formed of a parafilm was attached to the immunotube. Then, the immunotube was rotated upside down in a rotator for ten minutes.

The immunotube was left at rest at room temperature for one hour.

The inside of the immunotube was washed ten times with PBS containing 0.05% Tween 20. Hereinafter, such PBS is referred to as "PBST".

The inside of the immunotube was filled with PBST. Subsequently, the immunotube was left at rest for ten minutes. Then, the inside of the immunotube was washed ten times with PBST.

In order to extract phages each of which displays the VHH antibody bound to the NP antigen, a 100 mM trimethylamine solution (1 milliliter) was injected into the immunotube.

A lid formed of a parafilm was attached to the immunotube. Then, the immunotube was rotated upside down in a rotator for ten minutes.

In order to neutralize the solution, the solution was moved to a tube containing 1 mL of 0.5 M Tris/HCl (pH: 6.8). Again, the extraction of the phage was repeated using a 100 mM trimethylamine solution (1 milliliter). In this way, 3 mL of an extraction liquid was obtained.

The extraction liquid (1 mL) was mixed with 9 mL of *coli* bacteria HST02. The mixture solution was left at rest for one hour at a temperature of 30 degrees Celsius.

In order to count the number of colonies, 10 microliters of the mixture solution containing the *coli* bacteria HST02 was distributed onto a small plate including a 2TYA culture medium (10 milliliters/plate).

The rest of the mixture solution was subjected to centrifugation. The supernatant was removed, and the precipitate was distributed onto a large plate including a 2TYA culture medium (40 milliliters/plate). These two plates were left at rest overnight at a temperature of 30 degrees Celsius. In this way, first panning was conducted.

Second panning was conducted identically to the procedure of the first panning. In other words, the panning was repeated. In this way, the monoclonal phages on which the VHH antibody was displayed were purified.

After the second panning, a colony of the *coli* bacteria was picked up with a toothpick. The picked-up colony was put on one well of 96-flat-bottom plate. This was repeated. One well contained 200 microliters of a 2YTAG culture medium.

The solutions included in the wells were stirred at a rotation speed of 213 rpm at a temperature of 30 degrees Celsius.

The solution (50 microliters) containing grown *coli* bacteria was collected. The collected solution was mixed with 50 microliters of a 2YTA culture medium included in a plate. The 2YTA culture medium contained helper phages such that the multiplicity of infection was set to be 20. The solution was left at rest at a temperature of 37 degrees Celsius for forty minutes.

The plate including the 2YTA culture medium was subjected to centrifugation at 1,800 rpm for twenty minutes. The supernatant was removed. The precipitate contained the *coli* bacteria. The precipitate was mixed with 200 microliters of a 2YTAK culture medium. The mixture solution was left at rest overnight at a temperature of 30 degrees Celsius.

The mixture solution was subjected to centrifugation at 1,800 rpm for twenty minutes. The supernatant containing the *coli* bacteria was collected.

(C) Qualitative Evaluation of Phage-Displayed VHH Antibody and Antigen by ELISA

An intranuclear protein solution having a concentration of 2 micrograms/milliliter was injected as an antigen into each of the wells of a 96-well plate (available from Thermo scientific company, trade name: maxisorp). The volume of the intranuclear protein solution in each well was 50 microliters. The 96-well plate was left at rest overnight at a temperature of 4 degrees Celsius. In this way, the NP antigen was immobilized in each well.

Each of the wells was washed three times with PBS. Then, PBS containing 3% skim milk (available from Wako Pure Chemical Industries, Ltd.) was injected into each well (200 microliters/well). The 96-well plate was left at rest at room temperature for one hour. In this way, the intranuclear protein was blocked in each well. Subsequently, each well was washed three times with PBS.

The monoclonal phages each of which displays the VHH antibody were injected into each well (50 microliters/well). Then, the 96-well plate was left at rest for one hour. In this way, the phages reacted with the NP antigen.

Each well was washed three times with PBST. Then, an anti-M13 antibody (available from ABCAM company, trade name; ab50370, 10,000-fold dilution) was injected into each well (50 microliters/well). Then, each well was washed three times with PBST.

A color-producing agent (available from Thermo Scientific, trade name: 1-step ultra TMB-ELISA) was injected into each well (50 microliters/well). The 96-well plate was left at rest for two minutes to cause the color-producing agent to react with the antibody.

A sulfuric acid aqueous solution (normal, i.e., 1 N) was injected into each well at a concentration of 50 microliters/well to cease the reaction.

The absorbance of the solution at a wavelength of 450 nanometers was measured.

Fourteen wells each having good absorbance measurement result were selected. The DNA sequences included in the phages contained in the selected fourteen wells were analyzed by Greiner Company. The analysis results of the DNA sequences will be described below. The following one DNA sequence was found.

```
                                              (SEQ ID NO: 18)
CAGGTGCAGCTCGTGGAGTCTGGGGGGGGATTGGTGCAGACTGGGGGCCCG

CTGAGACTCTCCTGCGCAGTCTCTGATCGCACCGACAGTAACTATGCCATG

GGCTGGTTCCGCCAGGCTCCAGGGAAGGAGCGTGAGTTTGTAGCAGCTATT

AGCGGCACTGGTTATGTCACTGGCTATGCAGACTCCGCGAGGAATCGCTTC

ACCCTCTCCAGAGACAACGGCAAGAACGCGGTGTATCTGCAAATGAACAGC

CTGGAACCTGCGGACACGGCCGTTTATTACTGTGCAGCCACATCAGATCAA

CGCTATCCTGGTCCTCGCTCCTCGGGATATGACTACTGGGGCCAGGGGACC

CAGGTCACCGTCTCCTCA
```

The protein synthesized from the DNA sequence represented by SEQ ID NO: 18 consists of the following amino acid sequence.

```
                                    (SEQ ID NO: 8)
QVQLVESGGGLVQTGGPLRLSCAVSDRTDSNYAMGWERQAPGKEREEVAAI

SGTGYVTGYADSARNRFTLSRDNGKNAVYLQMNSLEPADTAVYYCAATSDQ

RYPGPRSSGYDYWGQGTQVTVSS
```

(Expression of Anti-NP VHH Antibody)

Figure 2:
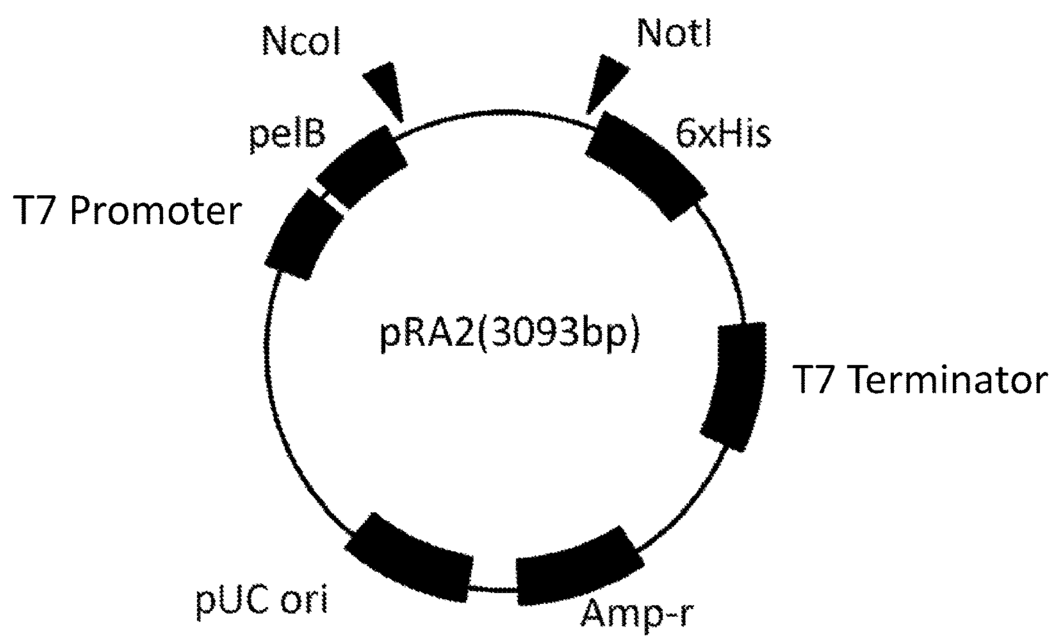
FIG. 2 shows a vector map used to express the VHH antibody.
Figure 3A:
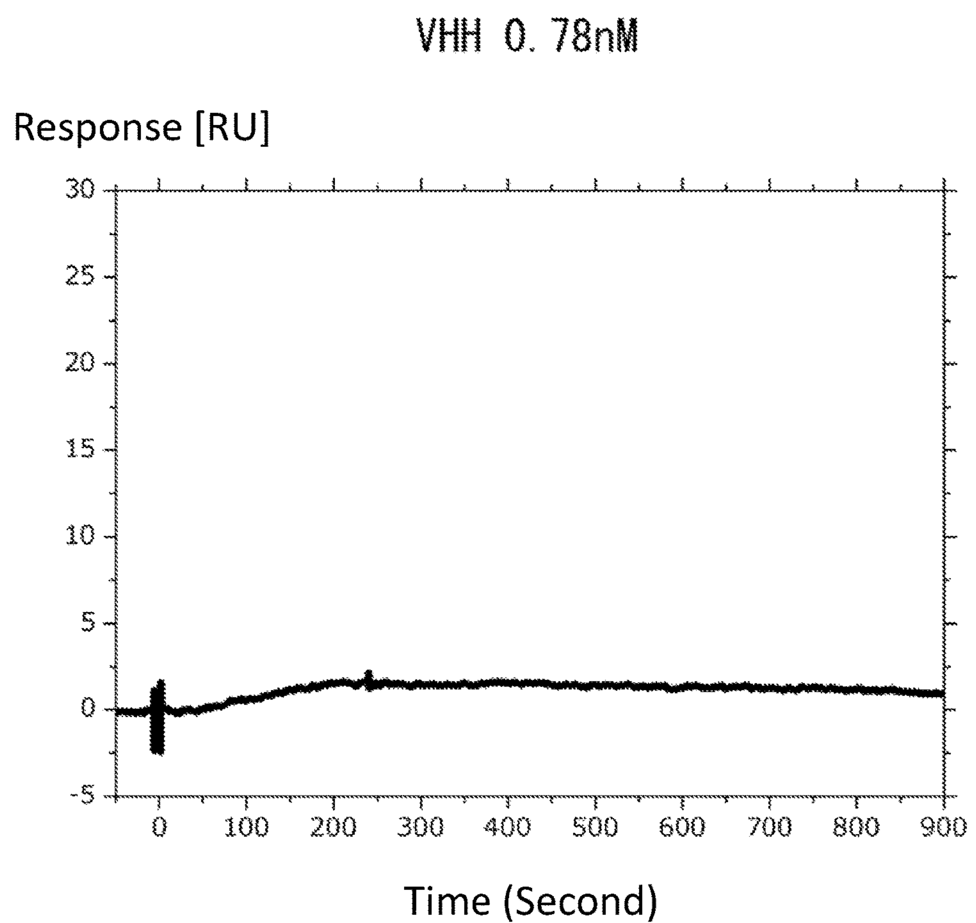
FIG. 3A is a graph showing a SPR evaluation result of the binding ability of the VHH antibody (concentration: 0.78 nM) including the amino acid sequence represented by SEQ ID NO: 8 to a recombinant intranuclear protein.
Figure 3B:
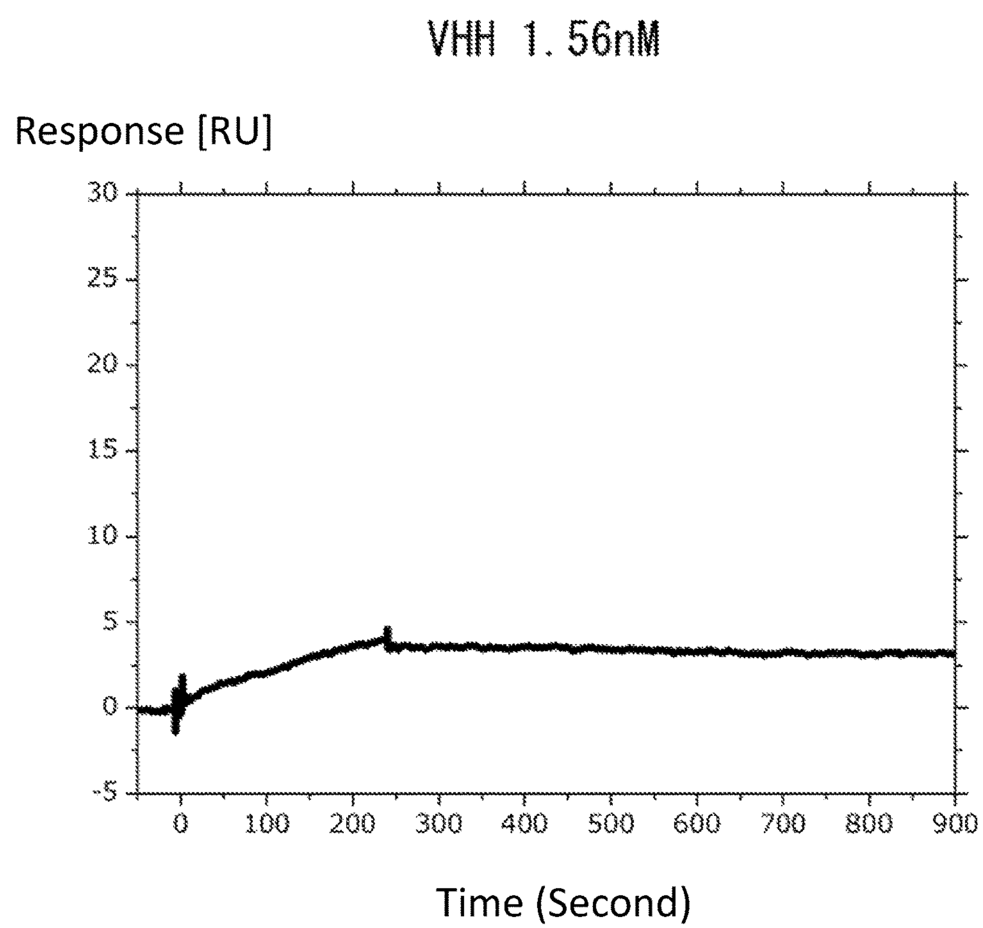
FIG. 3B is a graph showing a SPR evaluation result of the binding ability of the VHH antibody (concentration: 1.56 nM) including the amino acid sequence represented by SEQ ID NO: 8 to the recombinant intranuclear protein.
Figure 3C:
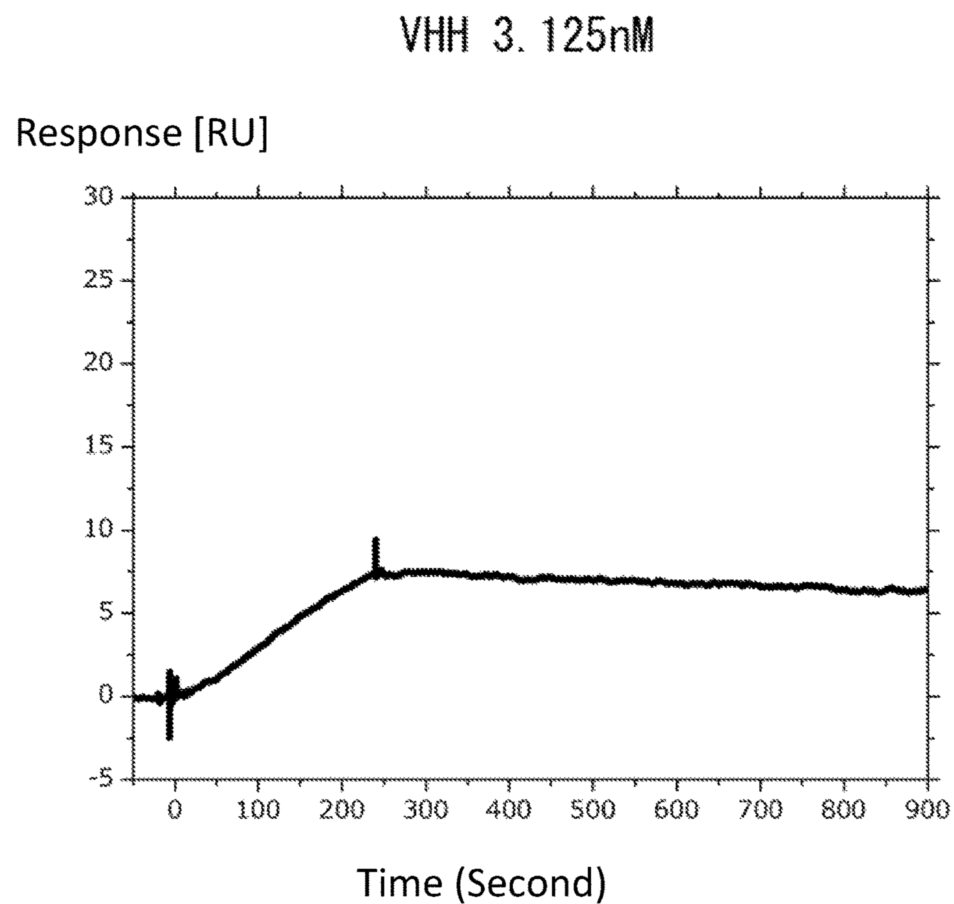
FIG. 3C is a graph showing a SPR evaluation result of the binding ability of the VHH antibody (concentration: 3.125 nM) including the amino acid sequence represented by SEQ ID NO: 8 to the recombinant intranuclear protein.
Figure 3D:
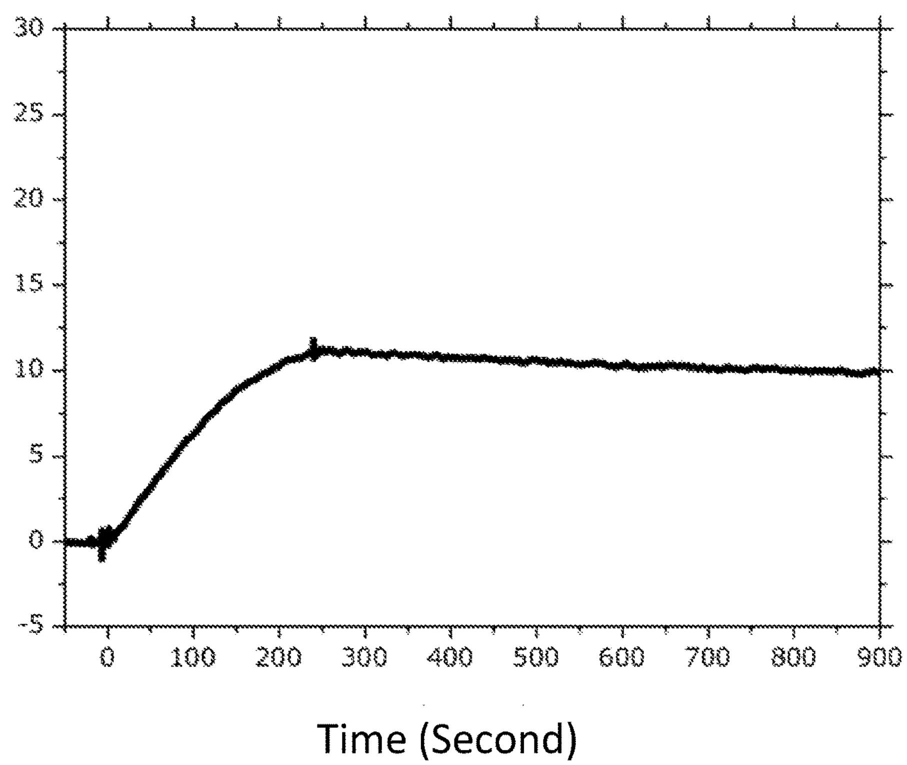
FIG. 3D is a graph showing a SPR evaluation result of the binding ability of the VHH antibody (concentration: 6.25 nM) including the amino acid sequence represented by SEQ ID NO: 8 to the recombinant intranuclear protein.
Figure 3E:
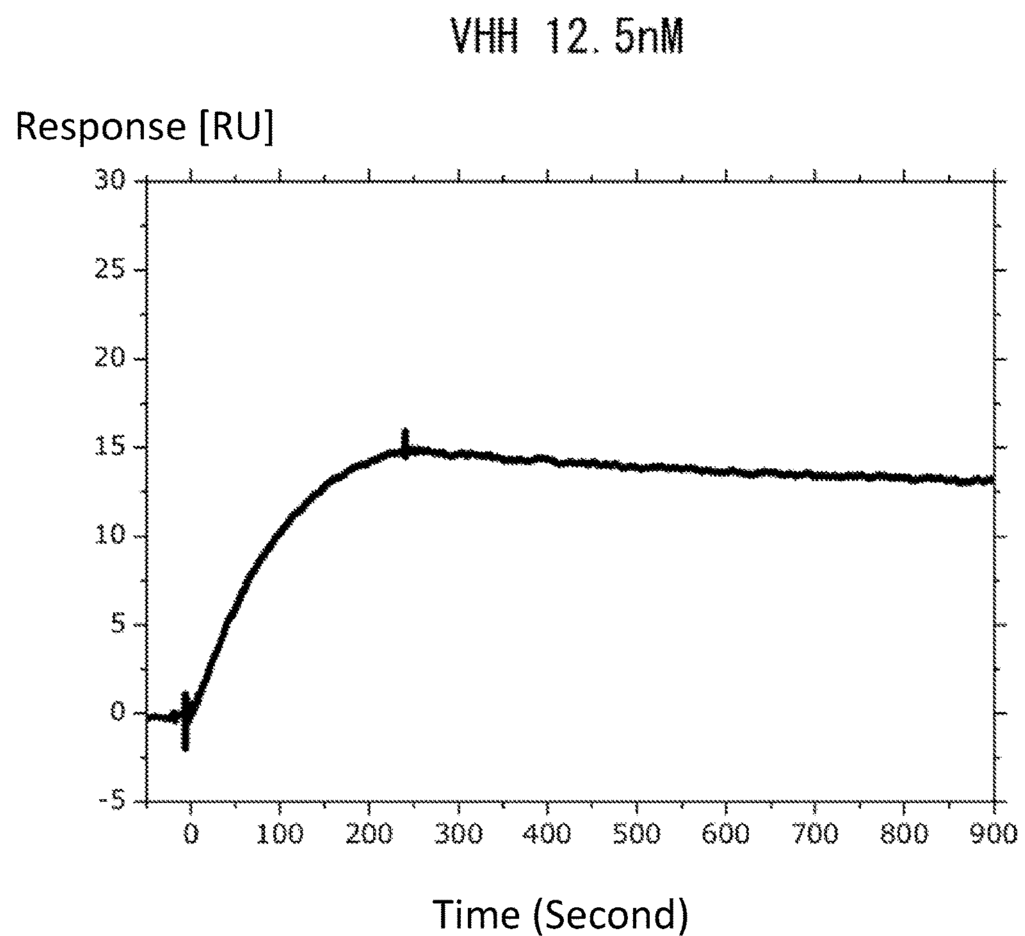
FIG. 3E is a graph showing a SPR evaluation result of the binding ability of the VHH antibody (concentration: 12.5 nM) including the amino acid sequence represented by SEQ ID NO: 8 to the recombinant intranuclear protein.
Figure 3F:
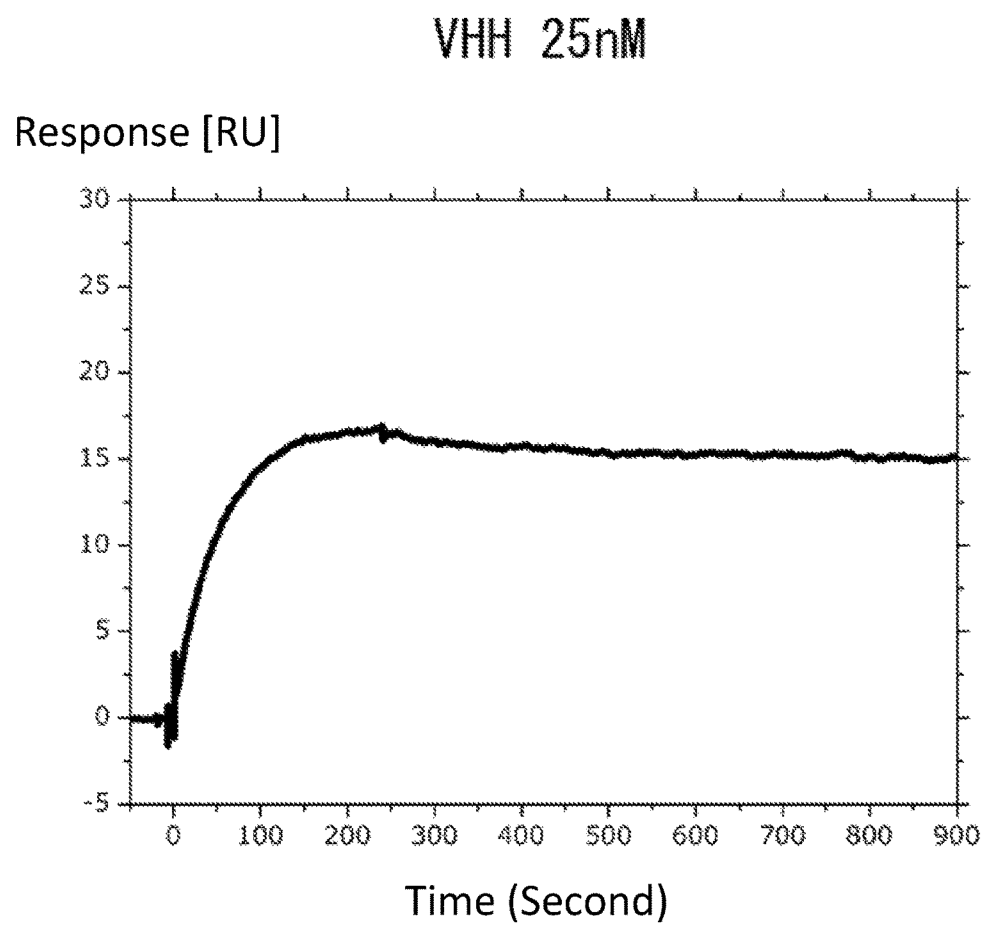
FIG. 3F is a graph showing a SPR evaluation result of the binding ability of the VHH antibody (concentration: 25 nM) including the amino acid sequence represented by SEQ ID NO: 8 to the recombinant intranuclear protein.
Figure 4A:
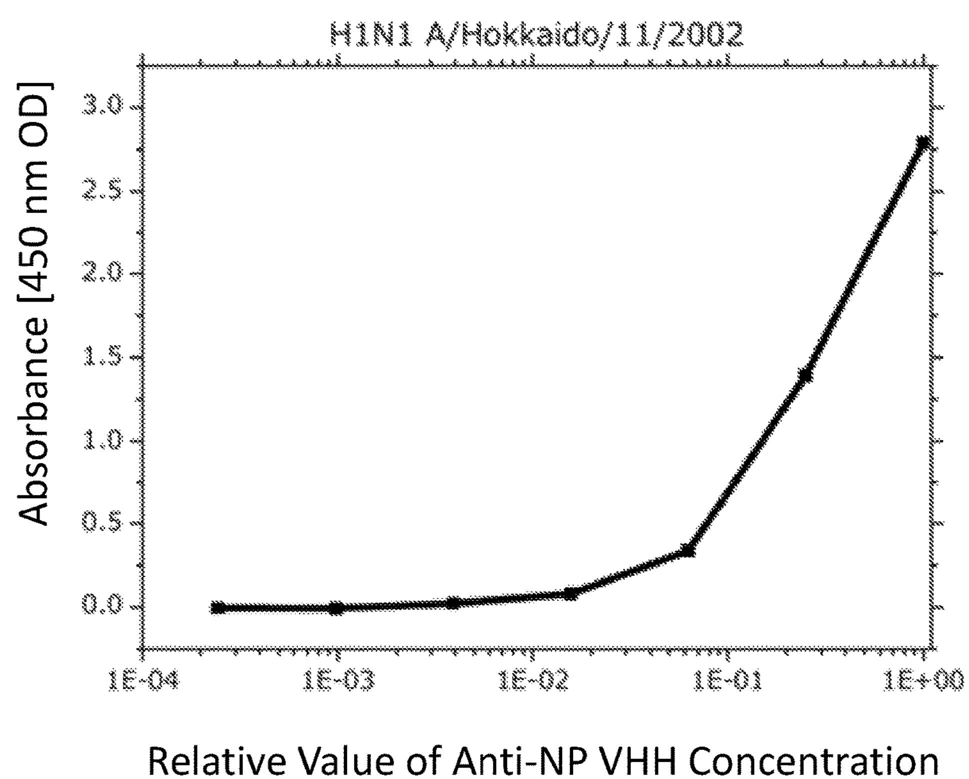
FIG. 4A is a graph showing a measurement result of a cross reactivity of the VHH antibody including the amino acid sequence represented by SEQ ID NO: 8 with a type-A influenza virus H1N1 A/Hokkaido/11/2002.
Figure 4B:
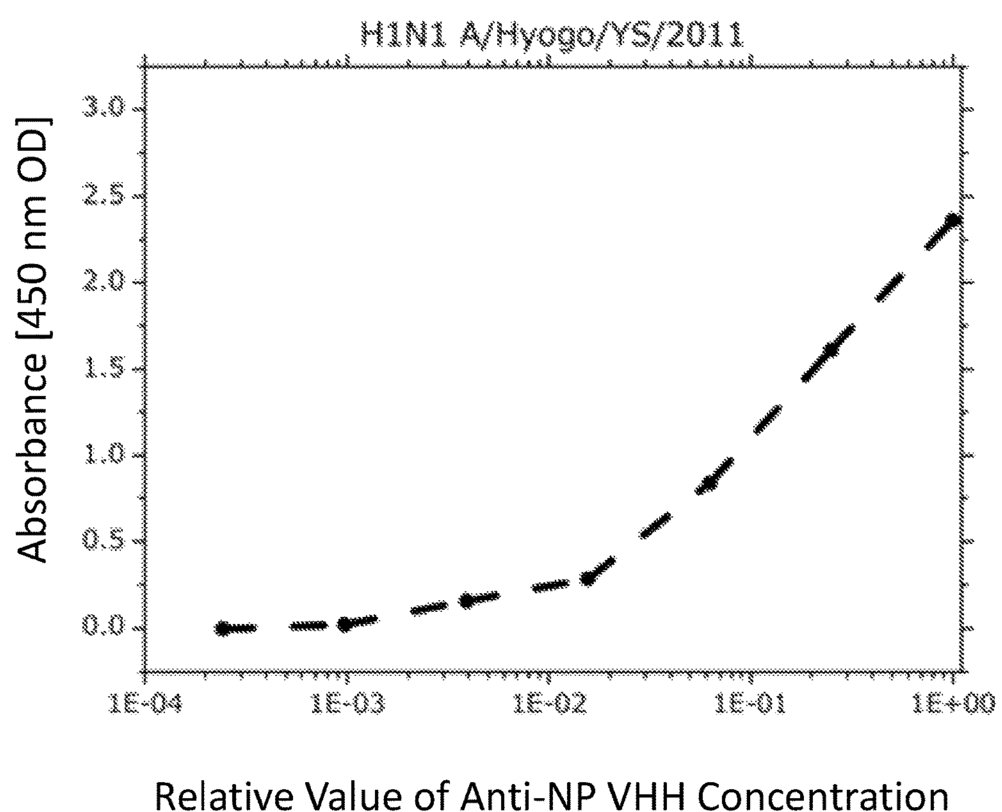
FIG. 4B is a graph showing a measurement result of a cross reactivity of the VHH antibody including the amino acid sequence represented by SEQ ID NO: 8 with a type-A influenza virus H1N1 A/Hyogo/YS/2011.
Figure 4C:
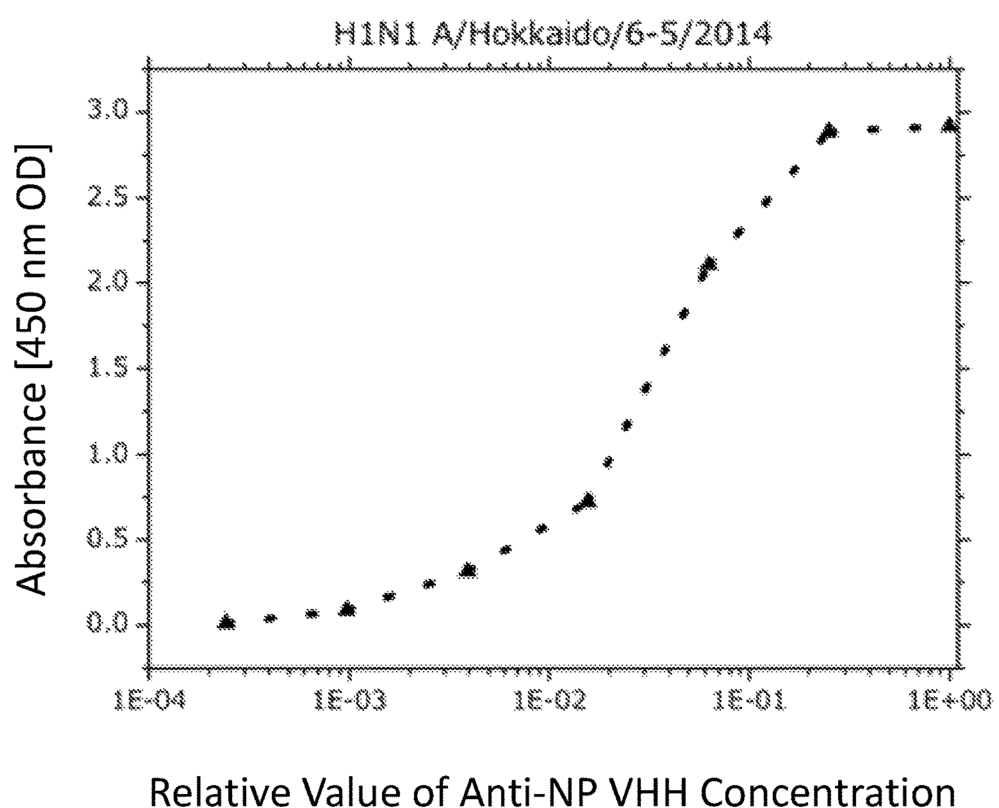
FIG. 4C is a graph showing a measurement result of a cross reactivity of the VHH antibody including the amino acid sequence represented by SEQ ID NO: 8 with a type-A influenza virus H1N1 A/Hokkaido/6-5/2014.
Figure 4D:
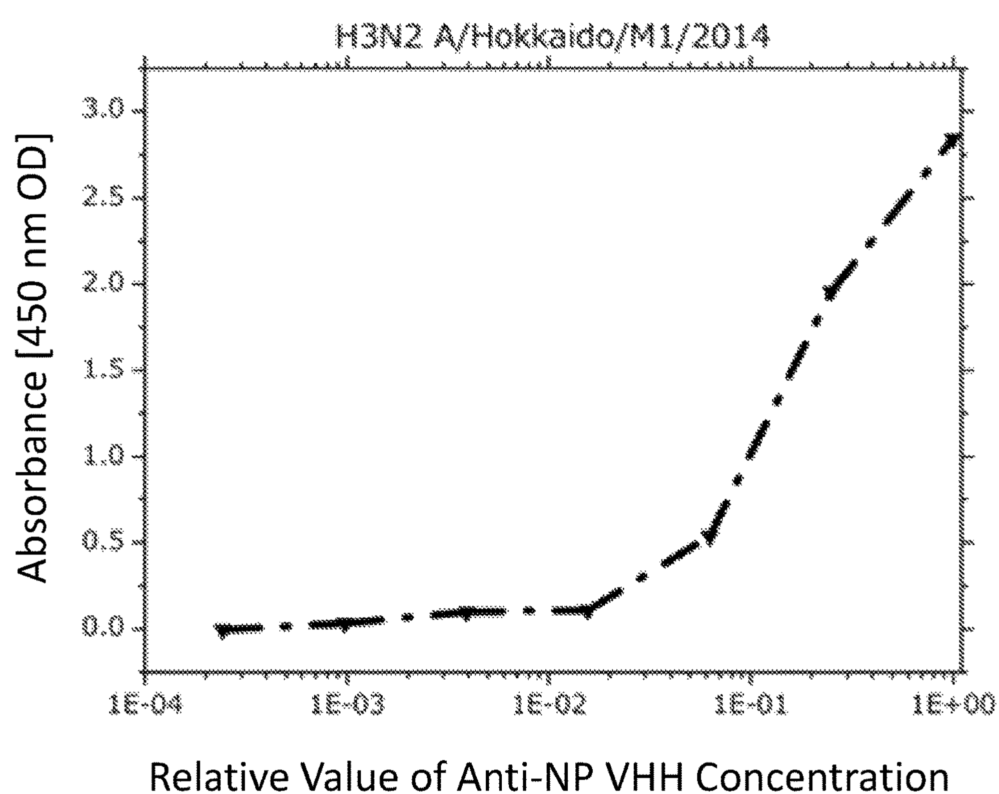
FIG. 4D is a graph showing a measurement result of a cross reactivity of the VHH antibody including the amino acid sequence represented by SEQ ID NO: 8 with a type-A influenza virus H3N2 A/Hokkaido/M1/2014.
Figure 4E:
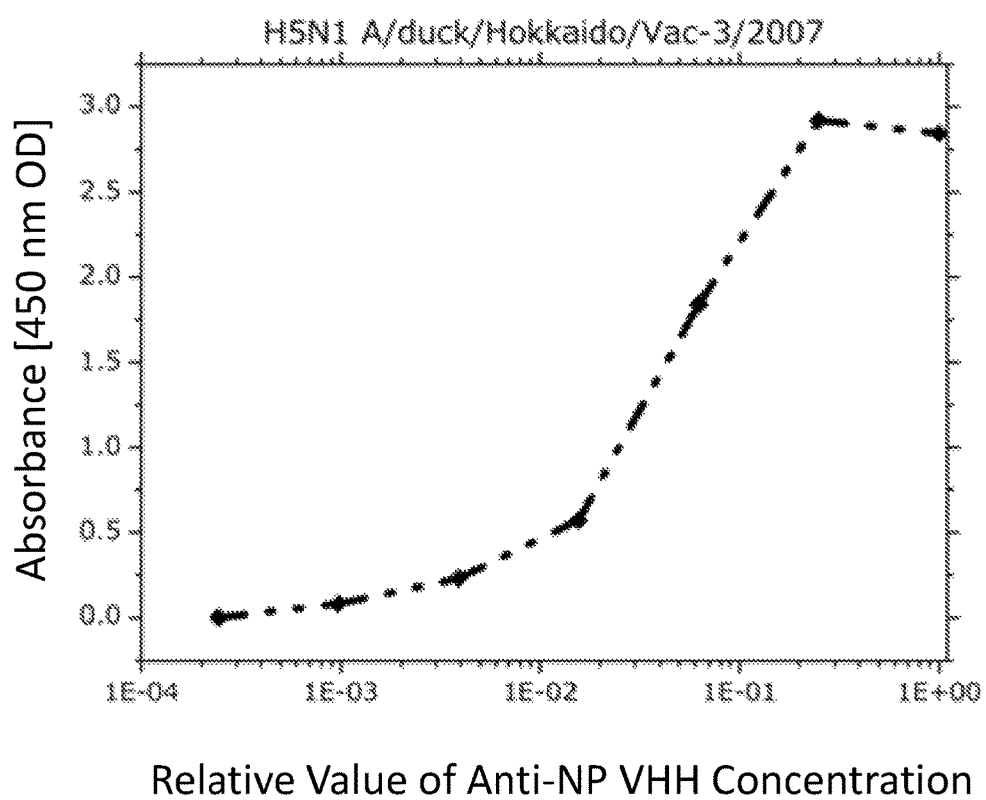
FIG. 4E is a graph showing a measurement result of a cross reactivity of the VHH antibody including the amino acid sequence represented by SEQ ID NO: 8 with a type-A influenza virus H5N1 A/duck/Hokkaido/Vac-3/2007.
Figure 4F:
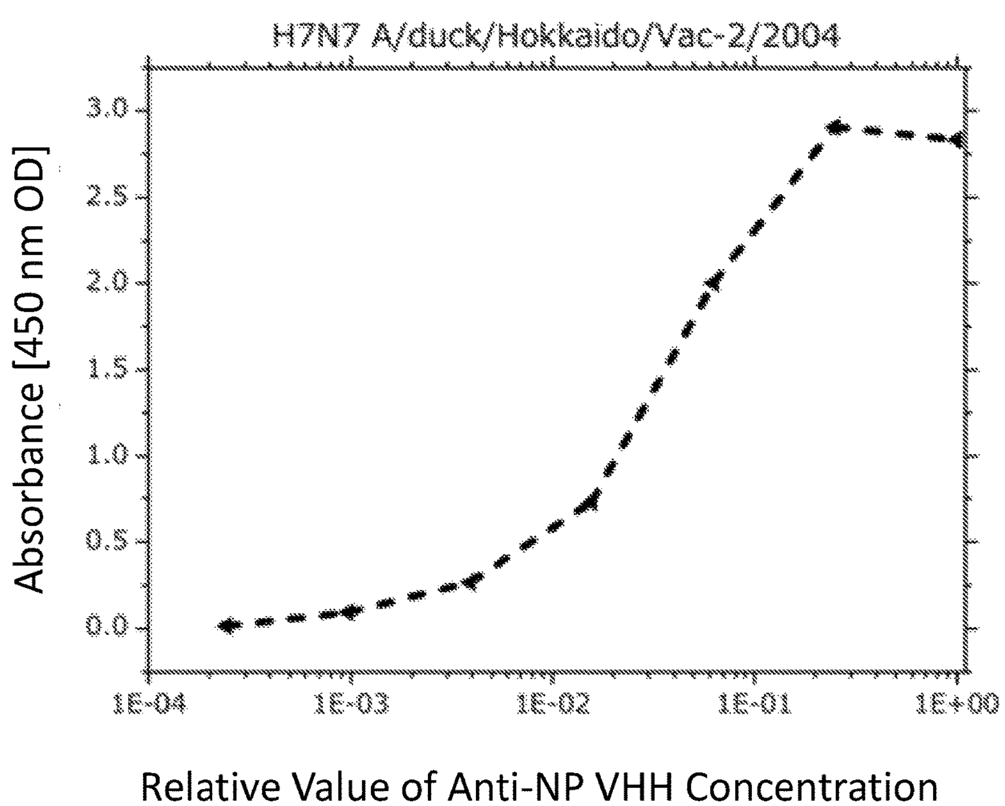
FIG. 4F is a graph showing a measurement result of a cross reactivity of the VHH antibody including the amino acid sequence represented by SEQ ID NO: 8 with a type-A influenza virus H7N7 A/duck/Hokkaido/Vac-2/2004.
Figure 4G:
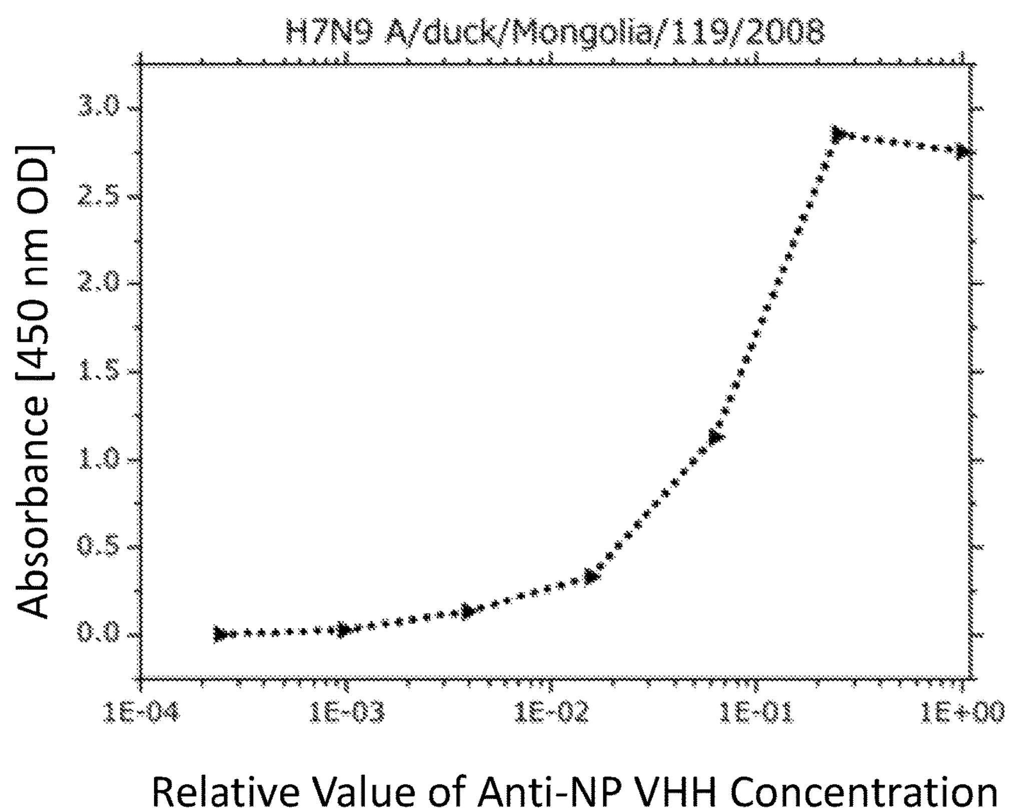
FIG. 4G is a graph showing a measurement result of a cross reactivity of the VHH antibody including the amino acid sequence represented by SEQ ID NO: 8 with a type-A influenza virus H7N9 A/duck/Mongolia/119/2008.

A vector pRA2(+) was used as an expression vector (see FIG. 2). The vector pRA2(+) was purchased from Merck Millipore Company. Using In-Fusion HD Cloning Kit (available from Takara Bio Inc.), the VHH sequence was ligated into a vector pRA2(+). Hereinafter, the ligation process will be described in more detail.

First, a VHH antibody gene fragment was amplified by the PCR method using the following two primers (SEQ ID NO: 19 and SEQ ID NO: 20) from the plasmid Vector 1 in which the VHH antibody gene fragment included in the gene library of the VHH antibody was ligated. In this way, the following one DNA (SEQ ID NO: 21) including a gene sequence coding for the amino acid sequence represented by the SEQ ID NO: 8 was obtained.

```
Primer 1:
                                    (SEQ ID NO: 19)
5'-CAGCCGGCCATGGCTCAGGTGCAGCTCGTGGAGTCTGG-3'

Primer 2:
                                    (SEQ ID NO: 20)
5'-ATGGTGTGCGGCCGCTGAGGAGACGGTGACCTGGGTCC-3'

                                    (SEQ ID NO: 21)
5'-CAGCCGGCCATGGCTCAGGTGCAGCTCGTGGAGTCTGGGGGGGGATTG

GTGCAGACTGGGGGCCCGCTGAGACTCTCCTGCGCAGTCTCTGATCGCACC

GACAGTAACTATGCCATGGGCTGGTTCCGCCAGGCTCCAGGGAAGGAGCGT

GAGTTTGTAGCAGCTATTAGCGGCACTGGTTATGTCACTGGCTATGCAGAC

TCCGCGAGGAATCGCTTCACCCTCTCCAGAGACAACGGCAAGAACGCGGTG

TATCTGCAAATGAACAGCCTGGAACCTGCGGACACGGCCGTTTATTACTGT

GCAGCCACATCAGATCAACGCTATCCTGGTCCTCGCTCCTCGGGATATGAC

TACTGGGGCCAGGGGACCCAGGTCACCGTCTCCTCAGCGGCCGCACACCA

T-3'
```

On the other hand, a part of the base sequence included in the vector pRA2 was amplified by a PCR method using the following two primers (SEQ ID NO: 22 and SEQ ID NO: 23). In this way, a DNA (SEQ ID NO: 25) was obtained.

```
Primer 1:
                                    (SEQ ID NO: 22)
5'-GCGGCCGCACACCATCATCACCACCATTAATAG-3'

Primer 2:
                                    (SEQ ID NO: 23)
5'-AGCCATGGCCGGCTGGGCCGCGAGTAATAAC-3'

                                    (SEQ ID NO: 25)
GCGGCCGCACACCATCATCACCACCATTAATAGcactagtcaagaggatcc

ggctgctaacaaagcccgaaaggaagctgagttggctgctgccaccgctga

gcaataactagcataaccccttggggcctctaaacgggtcttgaggggttt
```

-continued

```
tttgctgaaaggaggaactatatccggatgaattccgtgtattctatagtg

tcacctaaatcgtatgtgtatgatacataaggttatgtattaattgtagcc

gcgttctaacgacaatatgtacaagcctaattgtgtagcatctggcttact

gaagcagaccctatcatctctctcgtaaactgccgtcagagtcggtttggt

tggacgaaccttctgagtttctggtaacgccgtcccgcacccggaaatggt

cagcgaaccaatcagcagggtcatcgctagccagatcctctacgccggacg

catcgtggccggcatcaccggcgccacaggtgcggttgctggcgcctatat

cgccgacatcaccgatggggaagatcgggctcgccacttcgggctcatgag

cgcttgtttcggcgtgggtatggtggcaggccccgtggccgggggactgtt

gggcgccatctccttgcatgcaccattccttgcggcggcggtgctcaacgg

cctcaacctactactgggctgcttcctaatgcaggagtcgcataagggaga

gcgtcgaatggtgcactctcagtacaatctgctctgatgccgcatagttaa

gccagccccgacacccgccaacacccgctgacgcgccctgacgggcttgtc

tgctcccggcatccgcttacagacaagctgtgaccgtctccgggagctgca

tgtgtcagaggttttcaccgtcatcaccgaaacgcgcgagacgaaagggcc

tcgtgatacgcctatttttataggttaatgtcatgataataatggtttctt

agacgtcaggtggcacttttcggggaaatgtgcgcggaacccctatttgtt

tatttttctaaatacattcaaatatgtatccgctcatgagacaataaccct

gataaatgcttcaataatattgaaaaaggaagagtatgagtattcaacatt

tccgtgtcgcccttattcccttttttgcggcattttgccttcctgtttttg

ctcacccagaaacgctggtgaaagtaaaagatgctgaagatcagttgggtg

cacgagtgggttacatcgaactggatctcaacagcggtaagatccttgaga

gttttcgccccgaagaacgttttccaatgatgagcacttttaaagttctgc

tatgtggcgcggtattatcccgtattgacgccgggcaagagcaactcggtc

gccgcatacactattctcagaatgacttggttgagtactcaccagtcacag

aaaagcatcttacggatggcatgacagtaagagaattatgcagtgctgcca

taaccatgagtgataacactgcggccaacttacttctgacaacgatcggag

gaccgaaggagctaaccgcttttttgcacaacatgggggatcatgtaactc

gccttgatcgttgggaaccggagctgaatgaagccataccaaacgacgagc

gtgacaccacgatgcctgtagcaatggcaacaacgttgcgcaaactattaa

ctggcgaactacttactctagcttcccggcaacaattaatagactggatgg

aggcggataaagttgcaggaccacttctgcgctcggcccttccggctggct

ggtttattgctgataaatctggagccggtgagcgtgggtctcgcggtatca

ttgcagcactggggccagatggtaagccctcccgtatcgtagttatctaca

cgacggggagtcaggcaactatggatgaacgaaatagacagatcgctgaga

taggtgcctcactgattaagcattggtaactgtcagaccaagtttactcat

atatactttagattgatttaaaacttcatttttaatttaaaaggatctagg

tgaagatcctttttgataatctcatgaccaaaatcccttaacgtgagtttt

cgttccactgagcgtcagaccccgtagaaaagatcaaaggatcttcttgag

atcctttttttctgcgcgtaatctgctgcttgcaaacaaaaaaaccaccgc
```

-continued

```
taccagcggtggtttgtttgccggatcaagagctaccaactctttttccga

aggtaactggcttcagcagagcgcagataccaaatactgttcttctagtgt

agccgtagttaggccaccacttcaagaactctgtagcaccgcctacatacc

tcgctctgctaatcctgttaccagtggctgctgccagtggcgataagtcgt

gtcttaccgggttggactcaagacgatagttaccggataaggcgcagcggt

cgggctgaacggggggttcgtgcacacagcccagcttggagcgaacgacct

acaccgaactgagatacctacagcgtgagctatgagaaagcgccacgcttc

ccgaagggagaaaggcggacaggtatccggtaagcggcagggtcggaacag

gagagcgcacgagggagcttccagggggaaacgcctggtatctttatagtc

ctgtcgggtttcgccacctctgacttgagcgtcgatttttgtgatgctcgt

caggggggcggagcctatggaaaaacgccagcaacgcggcctttttacggt

tcctggccttttgctggccttttgctcacatgttctttcctgcgttatccc

ctgattctgtggataaccgtattaccgcctttgagtgagctgataccgctc

gccgcagccgaacgaccgagcgcagcgagtcagtgagcgaggaagcggaag

agcgcccaatacgcaaaccgcctctccccgcgcgttggccgattcattaat

gcagctggcttatcgaaattaatacgactcactatagggagacccaagctt

tatttcaaggagacagtcataATGaaatacctattgcctacggcagccgct

ggattgttattactcgcggcccagccggccatggct
```

DNAs other than the following two DNAs (I) and (II) were fragmented with a restriction enzyme DpnI (available from TOYOBO). In other words, the following two DNAs (I) and (II) remained unchanged; however, the rest of the DNAs were fragmented.

(I) the DNA represented by SEQ ID NO: 21, and (II) the DNA represented by SEQ ID NO: 25.

The DNA represented by SEQ ID NO: 21 was fused with the DNA represented by the SEQ ID NO: 25 using In-Fusion HD Cloning Kit (available from Takara Bio Inc.). In this way, the VHH antibody gene fragment was ligated into the vector pRA2(+).

The ligation solution (10 microliters) and *coli* bacteria JM109 (available from Takara Bio, 100 microliters) were mixed on ice. The mixture solution was left at rest on the ice for thirty minutes. Then, the mixture solution was heated at a temperature of 42 degrees Celsius for forty five seconds. Finally, the mixture solution was left at rest on the ice for three minutes. This procedure is known as a general heat shock method.

After the incubation at a temperature of 37 degrees Celsius for one hour with shaking, the total amount of the mixture solution was distributed onto an LBA culture medium containing ampicillin at a concentration of 100 micrograms/milliliter. The LBA culture medium was left at rest overnight at a temperature of 37 degrees Celsius.

Three colonies were selected from among the colonies formed on the LBA culture medium. The selected three colonies were incubated overnight in the LBA culture medium (3 milliliters).

The plasmids contained in the incubated *coli* bacteria were extracted from the LBA culture medium using a plasmid extraction kit (available from Sigma, trade name: Gene Elute Plasmid Mini Kit). In order to confirm that the gene of the targeted VHH antibody was inserted in the plasmid, the sequence of the plasmid was analyzed by Greiner Company. For the analysis of the sequence, a general T7 promotor primer set was used.

Selected were plasmids which were confirmed through the analysis of the sequence to have been formed as planned.

*Coli* bacteria (Competent Cell BL21 (DE3) pLysS, available from Life Technologies Company) were transfected with the selected plasmids by a heat shock method.

An LBA culture medium (1 milliliter) was injected into the solution containing the transfected *coli* bacteria. Then, the *coli* bacteria were recovered at a temperature of 37 degrees Celsius for one hour, while shaken at 213 rpm.

Then, the *coli* bacteria solution was collected. The collected *coli* bacteria solution (1 milliliter) was distributed onto an LBA culture medium. The LBA culture medium was left at rest overnight at a temperature of 37 degrees Celsius.

One colony was selected from among the colonies formed in the LBA culture medium. The selected colony was picked up with a toothpick. The picked-up colony was incubated in an LBA culture medium (3 milliliters) at a temperature of 37 degrees Celsius, while shaken at 213 rpm. In this way, a culture liquid was obtained.

In addition, the culture liquid (3 milliliters) was mixed with an LBA culture medium (1, 000 milliliters). Until the absorbance of the mixture solution at a wavelength of 600 nanometers reached 0.6, the mixture solution was shaken at 120 rpm at a temperature of 28 degrees Celsius.

After the absorbance reached 0.6, an isopropylthiogalactoside solution (hereinafter, referred to as "IPTG solution") was added to the mixture solution. The final concentration of the IPTG solution was 0.5 mM. The *coli* bacteria contained in the mixture solution were incubated at a temperature of 20 degrees Celsius overnight. In order to collect the thus-incubated *coli* bacteria, the mixture solution was subjected to centrifugation at 6,000 rpm at a temperature of 4 degrees Celsius for ten minutes.

The collected *coli* bacteria were mixed with a mixture solvent containing 50 mM Tris-HCl, 500 mM NaCl, and 5 mM imidazole. The mixture solvent had a volume of 50 milliliters. The *coli* bacteria contained in the mixture solution were disintegrated with an ultrasonic wave.

The disintegration liquid containing *coli* bacteria was subjected to centrifugation at 40,000 g at a temperature of 4 degrees Celsius for thirty minutes to obtain an eluate. The supernatant was collected. The collected supernatant was filtered through a 0.45-micrometer filter.

The filtrate was purified with Ni-NTA-Agarose (available from QIAGEN) in accordance with recommended protocol. For the purification, an elution buffer having a total amount of 3 milliliters was used for 1 milliliter of Ni-NTA-Agarose.

Furthermore, the eluate containing the anti-NP antibody was purified with a column chromatograph (available from General Electric Company, trade name: Akta purifier). In this way, a solution containing the anti-NP antibody was obtained.

The anti-NP antibody contained in the thus-obtained solution was quantified with an absorption spectrometer (available from Scrum Inc., trade name: nanodrop) on the basis of the absorption measurement value at a wavelength of 280 nanometers. As a result, the concentration of the anti-NP antibody was 6.60 milligrams/milliliter.

(D-1) Surface Plasmon Resonance Evaluation of Anti-NP Antibody Using Recombinant NP The anti-NP antibody was evaluated as below with a recombinant NP and a surface plasmon resonance evaluation device. The details of the surface plasmon resonance (hereinafter, referred to as "SPR") will be described below.

SPR evaluation device: T200 (available from GE Healthcare)

Immobilization buffer: PBS containing 0.05% of Tween 20

Running buffer: PBS containing 0.05% of Tween 20

Sensor chip: CM5 (available from GE Healthcare)

Immobilization reagents: N-hydroxysuccinimide (NHS) and N-[3-(Dimethylamino)propyl]-N'-ethylcarbodiimide (EDC)

Anti-Flag antibody: Monoclonal ANTI-FLAG antibody (available from SIGMA)

NP: recombinant nucleoprotein (NP) protein derived from influenza virus H1N1 to which a Flag tag was fused and which was prepared using baculovirus The anti-Flag antibody was immobilized in accordance with the wizard included in the control software of the SPR evaluation device T200. For the immobilization of the anti-Flag antibody, an acetic acid solution having a pH of 5.0 was used.

The anti-NP antibody consisting of the amino acid sequence represented by SEQ ID NO: 8 was used as an analyte. In the first to sixth analyses, the concentrations of the anti-NP antibody contained in the running buffer were adjusted to 0.78 nM, 1.56 nM, 3.125 nM, 6.25 nM, 12.5 nM, and 25 nM, respectively. First, the recombinant intranuclear proteins were captured with the anti-Flag antibodies. Then, the anti-NP antibodies were supplied. In this way, the anti-NP antibodies were evaluated. FIGS. 3A-3F are graphs showing an evaluation result outputted from the SPR evaluation device T200. The dissociation constant Kd was calculated using the evaluation software (available from GE Healthcare). As a result, the dissociation constant Kd was 0.199 nM.

(D-2) Evaluation of Cross Reactivity to Other Influenza Virus Subtypes

Next, in order to evaluate binding ability of the VHH antibody including the amino acid sequence represented by SEQ ID NO: 8 with nucleoproteins (namely, NPs) derived from a type-A influenza virus subtypes H1N1 (A/Hokkaido/11/2002), H1N1 (A/Hyogo/YS/2011), H1N1 (A/Hokkaido/6-5/2014), H3N2 (A/Hokkaido/M1/2014), H5N1 (A/duck/Hokkaido/Vac-3/2007), H7N7 (A/duck/Hokkaido/Vac-2/2004), and H7N9 (A/duck/Mongolia/119/2008), the binding ability to a virus solution containing the intranuclear proteins was evaluated by an ELISA measurement method.

The virus solution including the intranuclear protein derived from the type-A influenza virus subtype H1N1 (A/Hokkaido/11/2002) was prepared. The virus solution was obtained from School/Faculty of Veternary Medicine, Hokkaido University.

Similarly, six virus solutions including the intranuclear proteins derived from the type-A influenza virus subtypes H1N1 (A/Hyogo/YS/2011), H1N1 (A/Hokkaido/6-5/2014), H3N2 (A/Hokkaido/M1/2014), H5N1 (A/duck/Hokkaido/Vac-3/2007), H7N7 (A/duck/Hokkaido/Vac-2/2004), and H7N9 (A/duck/Mongolia/119/2008) were prepared. The virus solutions were obtained from School/Faculty of Veternary Medicine, Hokkaido University.

Furthermore, a virus solution including the intranuclear protein derived from the type-B influenza virus (B/Hokkaido/30-4/2014) was prepared. The virus solution was obtained from School/Faculty of Veternary Medicine, Hokkaido University.

A part of a solution A (concentration 10 micrograms/milliliter) containing the VHH antibody including the amino acid sequence represented by SEQ ID NO: 8 was diluted 4-fold with a PBS containing both 3% skim milk (available from Wako Pure Chemical Industries, Ltd.) and 0.05% Tween 20. Hereinafter, the PBS containing both 3% skim milk and 0. 05% Tween 20 is referred to as "skim-milk-containing PBST". In this way, a diluted solution B (concentration: 2. 5 micrograms/milliliter) of the solution containing the VHH antibody including the amino acid sequence represented by SEQ ID NO: 8 was provided. This was repeated to provide a diluted solution C (concentration: 0.625 micrograms/milliliter), a diluted solution D (concentration: 0. 15625 micrograms/milliliter), a diluted solution E (concentration: 0.0390625 micrograms/milliliter), a diluted solution F (concentration: $9.76562\times10^{-4}$ micrograms/milliliter), and a diluted solution G (concentration: $2.44141\times10^{-4}$ micrograms/milliliter).

The virus solutions including the intranuclear proteins derived from the type-A influenza virus subtypes H1N1 (A/Hokkaido/11/2002), H1N1 (A/Hyogo/YS/2011), H1N1 (A/Hokkaido/6-5/2014), H3N2 (A/Hokkaido/M1/2014), H5N1 (A/duck/Hokkaido/Vac-3/2007), H7N7 (A/duck/Hokkaido/Vac-2/2004), H7N9 (A/duck/Mongolia/119/2008), and the type-B influenza virus (B/Hokkaido/30-4/2014) were injected into the wells of 96-well plate (Maxisorp, Nunc). Each of the wells contained 50 microliters of the solution. The 96-well plate was left at rest at room temperature for two hours to immobilize the virus in the wells.

The skim-milk-containing PBST was injected into each well to block the virus. The volume of the PBST injected into each well was 200 microliters. The 96-well plate was left at rest at room temperature for three hours.

PBST containing 0. 05% Tween 20 was injected into each well to wash the wells. The PBST had a pH of 7.4. The volume of the PBST injected into each well was 200 microliters. This was repeated three times.

Each of the diluted solutions of the VHH antibody including the amino acid sequence represented by SEQ ID NO: 8 included in the diluted solutions A-G was injected into each well. As a reference, the skim-milk-containing PBST was injected into another well. This well including the skim-milk-containing PBST only was used as a reference to remove a background in measurement. The volume of the solutions injected into each well was 50 microliters. The 96-well plate was left at rest at room temperature. In this way, the VHH antibodies included in the diluted solutions A-G were bound to the intranuclear protein contained in the wells. The 96-well plate was left at rest at room temperature for one hour.

PBST containing 0. 05% Tween 20 was injected into each well to wash the wells. The PBST had a pH of 7.4. The volume of the PBST injected into each well was 200 microliters. This was repeated five times.

Labelled antibodies (available from Medical and Biological laboratories Co., Ltd, trade name: Anti-His-tagmAb-HRP-DirecT) were diluted 10,000-fold with PBST containing 0.05% Tween 20. The thus-diluted labelled antibodies were injected into each well (50 microliters/well). Then, the 96-well plate was left at rest for one hour.

PBST containing 0. 05% Tween 20 was injected into each well to wash the wells. The PBST had a pH of 7.4. The volume of the PBST injected into each well was 200 microliters. This was repeated five times.

The color-producing agent (available from Thermo Scientific, trade name: 1-step ultra TMB-ELISA) was injected into each well (50 microliters/well). The 96-well plate was left at rest for thirty minutes to cause the color-producing agent to react with the antibody.

A color-stopping agent (available from ScyTek laboratories, trade name: TMB Stop Buffer) containing sulfuric acid and hydrochloric acid at a low concentration was injected into each well at a concentration of 50 microliters/well to cease the reaction.

The absorbance of the solution at a wavelength of 450 nanometers was measured. FIGS. 4A-4H are graphs showing the measurement results of the cross reaction of the VHH antibody including the amino acid sequence represented by SEQ ID NO: 8 with the type-A influenza virus subtypes H1N1 (A/Hokkaido/11/2002), H1N1 (A/Hyogo/YS/2011), H1N1 (A/Hokkaido/6-5/2014), H3N2 (A/Hokkaido/M1/2014), H5N1 (A/duck/Hokkaido/Vac-3/2007), H7N7 (A/duck/Hokkaido/Vac-2/2004), H7N9 (A/duck/Mongolia/119/2008), and the type-B influenza virus, respectively.

As understood from FIGS. 4A-4H, the VHH antibody including the amino acid sequence represented by SEQ ID NO: 8 has high cross reactivity with the intranuclear proteins derived from the type-A influenza virus subtypes H1N1 (A/Hokkaido/11/2002), H1N1 (A/Hyogo/YS/2011), H1N1 (A/Hokkaido/6-5/2014), H3N2 (A/Hokkaido/M1/2014), H5N1 (A/duck/Hokkaido/Vac-3/2007), H7N7 (A/duck/Hokkaido/Vac-2/2004), and H7N9 (A/duck/Mongolia/119/2008). On the other hand, the VHH antibody including the amino acid sequence represented by SEQ ID NO: 8 has low cross reactivity with the type-B influenza virus.

INDUSTRIAL APPLICABILITY

The present invention provides a novel antibody capable of binding to an intranuclear protein of an influenza virus, a composite, a detection device and method using the same.

The invention claimed is:

1. A single-domain antibody including an amino acid sequence, wherein the amino acid sequence includes, in an N- to C-direction, the following structural domains:

```
N-FR1-CDR1-FR2-CDR2-FR3-CDR3-FR4-C
```

wherein

FR denotes a framework region amino acid sequence and CDR denotes a complementary determining region amino acid sequence;

the CDR1 includes an amino acid sequence represented by SEQ ID NO: 1;

the CDR2 includes an amino acid sequence represented by SEQ ID NO: 2;

the CDR3 includes an amino acid sequence represented by SEQ ID NO: 3; and the single-domain antibody is capable of binding to an intranuclear protein of a type-A influenza virus.

2. The single-domain antibody according to claim 1, wherein the type-A influenza virus is at least one selected from the group consisting of type-A influenza virus subtypes H1N1, H3N2, H5N1, H7N7, and H7N9.

3. The single-domain antibody according to claim 1, wherein the FR1 includes the amino acid sequences represented by SEQ ID NO: 4;

the FR2 includes the amino acid sequences represented by SEQ ID NO: 5;

the FR3 includes the amino acid sequences represented by SEQ ID NO: 6; and the FR4 includes the amino acid sequences represented by SEQ ID NO: 7.

4. A composite containing:

a single-domain antibody according to claim 1, wherein the antibody is bound to at least one selected from the group consisting of a solid phase support and a labeled substance.

5. The composite according to claim 4, wherein the single-domain antibody is bound to the solid phase support; and the solid phase support is selected from the group consisting of a plate, a bead, a disk, a tube, a filter, and a film.

6. The composite according to claim 4, wherein the single-domain antibody is bound to the labeled substance; and the labeled substance is selected from the group consisting of a fluorescent substance, a luminescent substance, a dye, an enzyme, and a radioactive substance.

7. A detection device comprising:

a composite according to claim 4; and a detector;

wherein the detector detects a change of a physical amount based on an antigen-antibody reaction of the composite and the intranuclear protein which is contained in an analyte.

8. A detection method comprising:

(a) bringing a composite according to claim 4 into contact with an analyte; and (b) detecting a change of a physical amount based on an antigen-antibody reaction of the composite and the intranuclear protein which is contained in the analyte.

* * * * *

```
                    SEQUENCE LISTING

<160> NUMBER OF SEQ ID NOS: 25

<210> SEQ ID NO 1
<211> LENGTH: 10
<212> TYPE: PRT
<213> ORGANISM: Vicugna pacos

<400> SEQUENCE: 1

Asp Arg Thr Asp Ser Asn Tyr Ala Met Gly
1               5                   10


<210> SEQ ID NO 2
<211> LENGTH: 17
<212> TYPE: PRT
<213> ORGANISM: Vicugna pacos

<400> SEQUENCE: 2

Ala Ile Ser Gly Thr Gly Tyr Val Thr Gly Tyr Ala Asp Ser Ala Arg
1               5                   10                  15

Asn


<210> SEQ ID NO 3
<211> LENGTH: 16
<212> TYPE: PRT
<213> ORGANISM: Vicugna pacos

<400> SEQUENCE: 3

Thr Ser Asp Gln Arg Tyr Pro Gly Pro Arg Ser Ser Gly Tyr Asp Tyr
1               5                   10                  15


<210> SEQ ID NO 4
<211> LENGTH: 25
<212> TYPE: PRT
<213> ORGANISM: Vicugna pacos

<400> SEQUENCE: 4

Gln Val Gln Leu Val Glu Ser Gly Gly Gly Leu Val Gln Thr Gly Gly
1               5                   10                  15

Pro Leu Arg Leu Ser Cys Ala Val Ser
            20                  25


<210> SEQ ID NO 5
<211> LENGTH: 14
<212> TYPE: PRT
<213> ORGANISM: Vicugna pacos
```

<400> SEQUENCE: 5

```
Trp Phe Arg Gln Ala Pro Gly Lys Glu Arg Glu Phe Val Ala
1               5                   10
```

<210> SEQ ID NO 6
<211> LENGTH: 32
<212> TYPE: PRT
<213> ORGANISM: Vicugna pacos

<400> SEQUENCE: 6

```
Arg Phe Thr Leu Ser Arg Asp Asn Gly Lys Asn Ala Val Tyr Leu Gln
1               5                   10                  15

Met Asn Ser Leu Glu Pro Ala Asp Thr Ala Val Tyr Tyr Cys Ala Ala
            20                  25                  30
```

<210> SEQ ID NO 7
<211> LENGTH: 11
<212> TYPE: PRT
<213> ORGANISM: Vicugna pacos

<400> SEQUENCE: 7

```
Trp Gly Gln Gly Thr Gln Val Thr Val Ser Ser
1               5                   10
```

<210> SEQ ID NO 8
<211> LENGTH: 125
<212> TYPE: PRT
<213> ORGANISM: Vicugna pacos

<400> SEQUENCE: 8

```
Gln Val Gln Leu Val Glu Ser Gly Gly Gly Leu Val Gln Thr Gly Gly
1               5                   10                  15

Pro Leu Arg Leu Ser Cys Ala Val Ser Asp Arg Thr Asp Ser Asn Tyr
            20                  25                  30

Ala Met Gly Trp Phe Arg Gln Ala Pro Gly Lys Glu Arg Glu Phe Val
        35                  40                  45

Ala Ala Ile Ser Gly Thr Gly Tyr Val Thr Gly Tyr Ala Asp Ser Ala
    50                  55                  60

Arg Asn Arg Phe Thr Leu Ser Arg Asp Asn Gly Lys Asn Ala Val Tyr
65                  70                  75                  80

Leu Gln Met Asn Ser Leu Glu Pro Ala Asp Thr Ala Val Tyr Tyr Cys
                85                  90                  95

Ala Ala Thr Ser Asp Gln Arg Tyr Pro Gly Pro Arg Ser Ser Gly Tyr
            100                 105                 110

Asp Tyr Trp Gly Gln Gly Thr Gln Val Thr Val Ser Ser
        115                 120                 125
```

<210> SEQ ID NO 9
<211> LENGTH: 15
<212> TYPE: DNA
<213> ORGANISM: Artificial Sequence
<220> FEATURE:
<223> OTHER INFORMATION: Primer

<400> SEQUENCE: 9

```
ggtggtcctg gctgc                                                    15
```

<210> SEQ ID NO 10
<211> LENGTH: 50
<212> TYPE: DNA
<213> ORGANISM: Artificial Sequence
<220> FEATURE:
<223> OTHER INFORMATION: Primer

<400> SEQUENCE: 10
ctgctcctcg cggcccagcc ggccatggct sagktgcagc tcgtggagtc 50

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
tggggtcttc gctgtggtgc g 21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
ttgtggtttt ggtgtcttgg g 21

<210> SEQ ID NO 13
<211> LENGTH: 45
<212> TYPE: DNA
<213> ORGANISM: Artificial Sequence
<220> FEATURE:
<223> OTHER INFORMATION: Primer

<400> SEQUENCE: 13
tttgctctgc ggccgcagag gccgtggggt cttcgctgtg gtgcg 45

<210> SEQ ID NO 14
<211> LENGTH: 46
<212> TYPE: DNA
<213> ORGANISM: Artificial Sequence
<220> FEATURE:
<223> OTHER INFORMATION: Primer

<400> SEQUENCE: 14
tttgctctgc ggccgcagag gccgattgtg gttttggtgt cttggg 46

<210> SEQ ID NO 15
<211> LENGTH: 13
<212> TYPE: DNA
<213> ORGANISM: Artificial Sequence
<220> FEATURE:
<223> OTHER INFORMATION: SfiI(a) site

<400> SEQUENCE: 15
ggcccagccg gcc 13

<210> SEQ ID NO 16
<211> LENGTH: 13
<212> TYPE: DNA
<213> ORGANISM: Artificial Sequence
<220> FEATURE:
<223> OTHER INFORMATION: SfiI(b) site

<400> SEQUENCE: 16
ggcctctgcg gcc 13

<210> SEQ ID NO 17
<211> LENGTH: 4057
<212> TYPE: DNA
<213> ORGANISM: Artificial Sequence
<220> FEATURE:
<223> OTHER INFORMATION: Plasmid Vector 1

<400> SEQUENCE: 17

```
gacgaaaggg cctcgtgata cgcctatttt tataggttaa tgtcatgata ataatggttt     60
cttagacgtc aggtggcact tttcggggaa atgtgcgcgg aacccctatt tgtttatttt    120
tctaaataca ttcaaatatg tatccgctca tgagacaata accctgataa atgcttcaat    180
aatattgaaa aaggaagagt atgagtattc aacatttccg tgtcgccctt attccctttt    240
ttgcggcatt ttgccttcct gtttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
```

```
acgcaattaa tgtgagttag ctcactcatt aggcacccca ggctttacac tttatgcttc   2160

cggctcgtat gttgtgtgga attgtgagcg gataacaatt tcacacagga aacagctatg   2220

accatgatta cgccaagctt cgaaggagac agtcataatg aaatacctgc tgccgaccgc   2280

tgctgctggt ctgctgctcc tcgcggccca gccggccatg gagctcaaga tgacacagac   2340

tacatcctcc ctgtcagcct ctctgggaga cagagtcacc atcagttgca gggcaagtca   2400

ggacattagc gattatttaa actggtatca gcagaaacca gatggaactg ttaaactcct   2460

gatctattac acatcaagtt tacactcagg agtcccatca aggttcagtg gcggtgggtc   2520

tggaacagat tattctctca ccattagcaa cctggagcaa gaagatattg ccacttactt   2580

ttgccaacag ggtaatacgc ttccgtggac gtttggtgga ggcaccaagc tggaaatcaa   2640

acgggctgat gctgcaccaa ctgtaggcct ctgcggccgc agagcaaaaa ctcatctcag   2700

aagaggatct gaatggggcc gcatagggtt ccggtgattt tgattatgaa aagatggcaa   2760

acgctaataa gggggctatg accgaaaatg ccgatgaaaa cgcgctacag tctgacgcta   2820

aaggcaaact tgattctgtc gctactgatt acggtgctgc tatcgatggt ttcattggtg   2880

acgtttccgg ccttgctaat ggtaatggtg ctactggtga ttttgctggc tctaattccc   2940

aaatggctca agtcggtgac ggtgataatt cacctttaat gaataatttc cgtcaatatt   3000

taccttccct ccctcaatcg gttgaatgtc gccctttgt ctttagcgct ggtaaaccat   3060

atgaattttc tattgattgt gacaaaataa acttattccg tggtgtcttt gcgtttcttt   3120

tatatgttgc cacctttatg tatgtatttt ctacgtttgc taacatactg cgtaataagg   3180

agtcttaata agaattcact ggccgtcgtt ttacaacgtc gtgactggga aaaccctggc   3240

gttacccaac ttaatcgcct tgcagcacat ccccctttcg ccagctggcg taatagcgaa   3300

gaggcccgca ccgatcgccc ttcccaacag ttgcgcagcc tgaatggcga atggcgcctg   3360

atgcggtatt ttctccttac gcatctgtgc ggtatttcac accgcatatg aaaattgtaa   3420

gcgttaatat tttgttaaaa ttcgcgttaa atttttgtta aatcagctca ttttttaacc   3480

aataggccga aatcggcaaa atcccttata aatcaaaaga atagaccgag atagggttga   3540

gtgttgttcc agtttggaac aagagtccac tattaaagaa cgtggactcc aacgtcaaag   3600

ggcgaaaaac cgtctatcag ggcgatggcc cactacgtga accatcaccc taatcaagtt   3660

ttttggggtc gaggtgccgt aaagcactaa atcggaaccc taaagggagc ccccgattta   3720

gagcttgacg gggaaagccg gcgaacgtgg cgagaaagga agggaagaaa gcgaaaggag   3780

cgggcgctag ggcgctggca agtgtagcgg tcacgctgcg cgtaaccacc acacccgccg   3840

cgcttaatgc gccgctacag ggcgcgtccc atatggtgca ctctcagtac aatctgctct   3900

gatgccgcat agttaagcca gccccgacac ccgccaacac ccgctgacgc gccctgacgg   3960

gcttgtctgc tcccggcatc cgcttacaga caagctgtga ccgtctccgg gagctgcatg   4020

tgtcagaggt tttcaccgtc atcaccgaaa cgcgcga                            4057
```

```
<210> SEQ ID NO 18
<211> LENGTH: 375
<212> TYPE: DNA
<213> ORGANISM: Artificial Sequence
<220> FEATURE:
<223> OTHER INFORMATION: DNA coding for anti-NP VHH antibody

<400> SEQUENCE: 18

caggtgcagc tcgtggagtc tgggggggga ttggtgcaga ctgggggccc gctgagactc     60
```

```
tcctgcgcag tctctgatcg caccgacagt aactatgcca tgggctggtt ccgccaggct    120

ccagggaagg agcgtgagtt tgtagcagct attagcggca ctggttatgt cactggctat    180

gcagactccg cgaggaatcg cttcaccctc tccagagaca acggcaagaa cgcggtgtat    240

ctgcaaatga acagcctgga acctgcggac acggccgttt attactgtgc agccacatca    300

gatcaacgct atcctggtcc tcgctcctcg ggatatgact actggggcca ggggacccag    360

gtcaccgtct cctca                                                     375


<210> SEQ ID NO 19
<211> LENGTH: 38
<212> TYPE: DNA
<213> ORGANISM: Artificial Sequence
<220> FEATURE:
<223> OTHER INFORMATION: Primer

<400> SEQUENCE: 19

cagccggcca tggctcaggt gcagctcgtg gagtctgg                             38


<210> SEQ ID NO 20
<211> LENGTH: 38
<212> TYPE: DNA
<213> ORGANISM: Artificial Sequence
<220> FEATURE:
<223> OTHER INFORMATION: Primer

<400> SEQUENCE: 20

atggtgtgcg gccgctgagg agacggtgac ctgggtcc                             38


<210> SEQ ID NO 21
<211> LENGTH: 405
<212> TYPE: DNA
<213> ORGANISM: Artificial Sequence
<220> FEATURE:
<223> OTHER INFORMATION: DNA including the gene sequence coding for the
      amino acid sequence represented by SEQ ID NO: 8

<400> SEQUENCE: 21

cagccggcca tggctcaggt gcagctcgtg gagtctgggg ggggattggt gcagactggg     60

ggcccgctga gactctcctg cgcagtctct gatcgcaccg acagtaacta tgccatgggc    120

tggttccgcc aggctccagg gaaggagcgt gagtttgtag cagctattag cggcactggt    180

tatgtcactg gctatgcaga ctccgcgagg aatcgcttca ccctctccag agacaacggc    240

aagaacgcgg tgtatctgca aatgaacagc ctggaacctg cggacacggc cgtttattac    300

tgtgcagcca catcagatca acgctatcct ggtcctcgct cctcgggata tgactactgg    360

ggccagggga cccaggtcac cgtctcctca gcggccgcac accat                    405


<210> SEQ ID NO 22
<211> LENGTH: 33
<212> TYPE: DNA
<213> ORGANISM: Artificial Sequence
<220> FEATURE:
<223> OTHER INFORMATION: Primer

<400> SEQUENCE: 22

gcggccgcac accatcatca ccaccattaa tag                                  33


<210> SEQ ID NO 23
<211> LENGTH: 31
<212> TYPE: DNA
<213> ORGANISM: Artificial Sequence
<220> FEATURE:
```

<223> OTHER INFORMATION: Primer

<400> SEQUENCE: 23
agccatggcc ggctgggccg cgagtaataa c 31

<210> SEQ ID NO 24
<211> LENGTH: 498
<212> TYPE: PRT
<213> ORGANISM: Artificial Sequence
<220> FEATURE:
<223> OTHER INFORMATION: Recombinant nuclear protein

<400> SEQUENCE: 24

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335
```

```
Ala Phe Glu Asp Leu Arg Val Leu Ser Phe Ile Lys Gly Thr Lys Val
            340                 345                 350

Leu Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Asn Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 25
<211> LENGTH: 3096
<212> TYPE: DNA
<213> ORGANISM: Artificial Sequence
<220> FEATURE:
<223> OTHER INFORMATION: DNA amplified from Vector pRA2

<400> SEQUENCE: 25

gcggccgcac accatcatca ccaccattaa tagcactagt caagaggatc cggctgctaa     60

caaagcccga aaggaagctg agttggctgc tgccaccgct gagcaataac tagcataacc    120

ccttggggcc tctaaacggg tcttgagggg ttttttgctg aaaggaggaa ctatatccgg    180

atgaattccg tgtattctat agtgtcacct aaatcgtatg tgtatgatac ataaggttat    240

gtattaattg tagccgcgtt ctaacgacaa tatgtacaag cctaattgtg tagcatctgg    300

cttactgaag cagaccctat catctctctc gtaaactgcc gtcagagtcg gtttggttgg    360

acgaaccttc tgagtttctg gtaacgccgt cccgcacccg gaaatggtca gcgaaccaat    420

cagcagggtc atcgctagcc agatcctcta cgccggacgc atcgtggccg gcatcaccgg    480

cgccacaggt gcggttgctg gcgcctatat cgccgacatc accgatgggg aagatcgggc    540

tcgccacttc gggctcatga gcgcttgttt cggcgtgggt atggtggcag gccccgtggc    600

cgggggactg ttgggcgcca tctccttgca tgcaccattc cttgcggcgg cggtgctcaa    660

cggcctcaac ctactactgg gctgcttcct aatgcaggag tcgcataagg gagagcgtcg    720

aatggtgcac tctcagtaca atctgctctg atgccgcata gttaagccag ccccgacacc    780

cgccaacacc cgctgacgcg ccctgacggg cttgtctgct cccggcatcc gcttacagac    840

aagctgtgac cgtctccggg agctgcatgt gtcagaggtt ttcaccgtca tcaccgaaac    900

gcgcgagacg aaagggcctc gtgatacgcc tatttttata ggttaatgtc atgataataa    960

tggtttctta gacgtcaggt ggcacttttc ggggaaatgt gcgcggaacc cctatttgtt   1020

tatttttcta aatacattca aatatgtatc cgctcatgag acaataaccc tgataaatgc   1080

ttcaataata ttgaaaaagg aagagtatga gtattcaaca tttccgtgtc gcccttattc   1140
```

```
cctttttgc ggcattttgc cttcctgttt ttgctcaccc agaaacgctg gtgaaagtaa   1200

aagatgctga agatcagttg ggtgcacgag tgggttacat cgaactggat ctcaacagcg   1260

gtaagatcct tgagagtttt cgccccgaag aacgttttcc aatgatgagc acttttaaag   1320

ttctgctatg tggcgcggta ttatcccgta ttgacgccgg gcaagagcaa ctcggtcgcc   1380

gcatacacta ttctcagaat gacttggttg agtactcacc agtcacagaa aagcatctta   1440

cggatggcat gacagtaaga gaattatgca gtgctgccat aaccatgagt gataacactg   1500

cggccaactt acttctgaca acgatcggag gaccgaagga gctaaccgct tttttgcaca   1560

acatggggga tcatgtaact cgccttgatc gttgggaacc ggagctgaat gaagccatac   1620

caaacgacga gcgtgacacc acgatgcctg tagcaatggc aacaacgttg cgcaaactat   1680

taactggcga actacttact ctagcttccc ggcaacaatt aatagactgg atggaggcgg   1740

ataaagttgc aggaccactt ctgcgctcgg cccttccggc tggctggttt attgctgata   1800

aatctggagc cggtgagcgt gggtctcgcg gtatcattgc agcactgggg ccagatggta   1860

agccctcccg tatcgtagtt atctacacga cggggagtca ggcaactatg gatgaacgaa   1920

atagacagat cgctgagata ggtgcctcac tgattaagca ttggtaactg tcagaccaag   1980

tttactcata tatactttag attgatttaa aacttcattt ttaatttaaa aggatctagg   2040

tgaagatcct ttttgataat ctcatgacca aaatccctta acgtgagttt tcgttccact   2100

gagcgtcaga ccccgtagaa aagatcaaag gatcttcttg agatcctttt tttctgcgcg   2160

taatctgctg cttgcaaaca aaaaaaccac cgctaccagc ggtggtttgt ttgccggatc   2220

aagagctacc aactcttttt ccgaaggtaa ctggcttcag cagagcgcag ataccaaata   2280

ctgttcttct agtgtagccg tagttaggcc accacttcaa gaactctgta gcaccgccta   2340

catacctcgc tctgctaatc ctgttaccag tggctgctgc cagtggcgat aagtcgtgtc   2400

ttaccgggtt ggactcaaga cgatagttac cggataaggc gcagcggtcg ggctgaacgg   2460

ggggttcgtg cacacagccc agcttggagc gaacgaccta caccgaactg agatacctac   2520

agcgtgagct atgagaaagc gccacgcttc ccgaagggag aaaggcggac aggtatccgg   2580

taagcggcag ggtcggaaca ggagagcgca cgagggagct tccaggggga aacgcctggt   2640

atctttatag tcctgtcggg tttcgccacc tctgacttga gcgtcgattt ttgtgatgct   2700

cgtcaggggg gcggagccta tggaaaaacg ccagcaacgc ggccttttta cggttcctgg   2760

ccttttgctg gccttttgct cacatgttct ttcctgcgtt atcccctgat tctgtggata   2820

accgtattac cgcctttgag tgagctgata ccgctcgccg cagccgaacg accgagcgca   2880

gcgagtcagt gagcgaggaa gcggaagagc gcccaatacg caaaccgcct ctccccgcgc   2940

gttggccgat tcattaatgc agctggctta tcgaaattaa tacgactcac tatagggaga   3000

cccaagcttt atttcaagga gacagtcata atgaaatacc tattgcctac ggcagccgct   3060

ggattgttat tactcgcggc ccagccggcc atggct                            3096
```